US00RE49353E

(19) United States
(12) Reissued Patent
Chen

(10) Patent Number: US RE49,353 E
(45) Date of Reissued Patent: Jan. 3, 2023

(54) ANTI-ANDROGENS FOR THE TREATMENT OF NON-METASTATIC CASTRATE-RESISTANT PROSTATE CANCER

(71) Applicant: Aragon Pharmaceuticals, Inc., Los Angeles, CA (US)

(72) Inventor: Isan Chen, San Diego, CA (US)

(73) Assignee: Aragon Pharmaceuticals, Inc., Los Angeles, CA (US)

(21) Appl. No.: 16/998,683

(22) Filed: Aug. 20, 2020

Related U.S. Patent Documents

Reissue of:
(64) Patent No.: 10,052,314
Issued: Aug. 21, 2018
Appl. No.: 15/851,444
Filed: Dec. 21, 2017

U.S. Applications:
(63) Continuation of application No. 14/034,460, filed on Sep. 23, 2013, now Pat. No. 9,884,054.

(60) Provisional application No. 61/705,900, filed on Sep. 26, 2012.

(51) Int. Cl.
*A61K 31/4439* (2006.01)
*A61K 31/00* (2006.01)
*A61K 31/4166* (2006.01)

(52) U.S. Cl.
CPC ..... *A61K 31/4439* (2013.01); *A61K 31/00* (2013.01); *A61K 31/4166* (2013.01); *H05K 999/99* (2013.01)

(58) Field of Classification Search
CPC ..... A61K 31/4439; A61K 31/00; A61K 31/4166; A61K 38/09; A61K 9/0053; A61K 9/20; A61K 9/48; H05K 999/99; A61P 5/02; A61P 5/28; A61P 13/08; A61P 35/00; A61P 37/00; A61P 43/00
See application file for complete search history.

(56) References Cited

U.S. PATENT DOCUMENTS 3,798,233 A 3/1974 Akiba et al.
3,823,240 A 7/1974 Sauli
3,984,430 A 10/1976 Curran
4,097,578 A 6/1978 Perronnet et al.
4,229,447 A 10/1980 Porter
4,234,736 A 11/1980 Bernauer et al.
4,304,782 A 12/1981 Dumont et al.
4,312,881 A 1/1982 Wootton
4,399,216 A 8/1983 Axel et al.
4,407,814 A 10/1983 Bernauer et al.
4,427,438 A 1/1984 Nagano et al.
4,473,393 A 9/1984 Nagpal
4,482,739 A 11/1984 Bernauer et al.
4,559,157 A 12/1985 Smith et al.
4,596,795 A 6/1986 Pitha
4,608,392 A 8/1986 Jacquet et al.
4,749,403 A 6/1988 Liebl et al.
4,755,386 A 7/1988 Hsiao et al.
4,820,508 A 4/1989 Wortzman
4,859,228 A 8/1989 Prisbylla
4,873,256 A 10/1989 Coussediere et al.
4,938,949 A 7/1990 Borch et al.
4,944,791 A 7/1990 Schroder et al.
4,992,478 A 2/1991 Geria
5,010,182 A 4/1991 Brake et al.
5,011,692 A 4/1991 Fujioka et al.
5,017,381 A 5/1991 Maruyama et al.
5,033,252 A 7/1991 Carter
5,052,558 A 10/1991 Carter
5,069,711 A 12/1991 Fischer et al.
5,071,773 A 12/1991 Evans et al.
5,166,358 A 11/1992 Seuron et al.
5,229,135 A 7/1993 Philippon et al.
5,323,907 A 6/1994 Kalvelage
5,411,981 A 5/1995 Gaillard-Kelly et al.
5,434,176 A 7/1995 Claussner et al.
5,554,607 A 9/1996 Elokdah et al.
5,556,983 A 9/1996 Claussner et al.
5,589,497 A 12/1996 Claussner et al.
5,614,620 A 3/1997 Liao et al.
5,627,201 A 5/1997 Gaillard-Kelly et al.
5,646,172 A 7/1997 Claussner et al.
5,656,651 A 8/1997 Sovak et al.
5,705,654 A 1/1998 Claussner et al.
5,726,061 A 3/1998 Robbins et al.
5,738,685 A 4/1998 Halm et al.
5,739,136 A 4/1998 Ellinwood, Jr. et al.
5,750,553 A 5/1998 Claussner et al.
5,783,707 A 7/1998 Elokdah et al.
RE35,956 E 11/1998 Gaillard-Kelly et al.
(Continued)

FOREIGN PATENT DOCUMENTS

AU 0217893 6/1958
AU 2013323861 A1 4/2015
(Continued)

OTHER PUBLICATIONS

Gocmen et al., In Vitro Investigation of the Antibacterial Effect of Ketamine; Upsala J Med Sci 113 (1) 2008: pp. 39-46.
Ryan et al., "Impact of prior ketoconazole therapy on response proportion to abiraterone acetate, a 17-alpha hydroxy lase C17,20-lyase inhibitor in castration resistant prostate cancer (CRPC)," J. Clin. Oncol. (Meeting abstracts), vol. 26 (May 20 Supplement), abstract No. 5018 (2008).
Visentin et al. Heparin is not required for detection of antibodies associated with heparin-induced thrombocytopenia/thrombosis. J Lab Clin Med 138, 22-31 (2001).
Sonpavde, "Abiraterone acetate for metastatic prostate cancer" Lancet Oncology (2012), vol. 12, Issue 10, pp. 958-959.
Tombal, Annals of Oncology 23(suppl 9):x251-x258, 2012.
U.S. Appl. Jung et al., filed Mar. 27, 2006., U.S. Appl. No. 60/785,978.
(Continued)

*Primary Examiner* — Jerry D Johnson
(74) *Attorney, Agent, or Firm* — BakerHostetler

(57) ABSTRACT

Described herein are methods of treating non-metastatic castrate-resistant prostate cancer with anti-androgens.

48 Claims, No Drawings

(56) References Cited

U.S. PATENT DOCUMENTS

| | | | |
|---|---|---|---|
| 5,837,284 | A | 11/1998 | Mehta et al. |
| 5,840,329 | A | 11/1998 | Bai |
| 5,958,936 | A | 9/1999 | Claussner et al. |
| 5,968,875 | A | 10/1999 | Bis et al. |
| 5,985,868 | A | 11/1999 | Gray |
| 6,107,488 | A | 8/2000 | Bouchet et al. |
| 6,172,076 | B1 | 1/2001 | Embrey et al. |
| 6,235,910 | B1 | 5/2001 | Beller et al. |
| 6,242,611 | B1 | 6/2001 | Claussner et al. |
| 6,307,030 | B1 | 10/2001 | French et al. |
| 6,350,763 | B1 | 2/2002 | Kelly et al. |
| 6,472,415 | B1 | 10/2002 | Sovak et al. |
| 6,479,063 | B2 | 11/2002 | Weisman et al. |
| 6,489,163 | B1 | 12/2002 | Roy et al. |
| 6,506,607 | B1 | 1/2003 | Shyjan |
| 6,710,037 | B2 | 3/2004 | Wang et al. |
| 6,828,471 | B2 | 12/2004 | Sawyers et al. |
| 7,271,188 | B2 | 9/2007 | Tachibana et al. |
| 7,709,517 | B2 | 5/2010 | Sawyers et al. |
| 8,110,594 | B2 | 2/2012 | Jung et al. |
| 8,183,274 | B2 | 5/2012 | Sawyers et al. |
| 8,445,507 | B2 | 5/2013 | Jung et al. |
| 8,461,343 | B2 | 6/2013 | Ouerfelli et al. |
| 8,470,829 | B2 | 6/2013 | Tachibana et al. |
| 8,648,105 | B2 | 2/2014 | Jung et al. |
| 8,802,689 | B2 | 8/2014 | Jung et al. |
| 8,841,081 | B2 | 9/2014 | Persson |
| 8,987,452 | B2 | 3/2015 | Ouerfelli et al. |
| 9,108,944 | B2 | 8/2015 | Smith et al. |
| 9,126,941 | B2 | 9/2015 | Sawyers et al. |
| 9,289,436 | B2 | 3/2016 | Szmulewitz et al. |
| 9,340,524 | B2 | 5/2016 | Chen |
| 9,388,159 | B2 | 7/2016 | Jung et al. |
| 9,415,085 | B2 | 8/2016 | Van Der Meulen et al. |
| 9,481,664 | B2 | 11/2016 | Smith et al. |
| 9,512,103 | B2 | 12/2016 | Ouerfelli et al. |
| 9,579,359 | B2 | 2/2017 | Olesen et al. |
| 9,675,586 | B2 | 6/2017 | Chow et al. |
| 9,877,999 | B2 | 1/2018 | Persson |
| 9,884,054 | B2 | 2/2018 | Chen |
| 9,987,261 | B2 | 6/2018 | Jung et al. |
| 10,052,314 | B2 | 8/2018 | Chen |
| 10,537,586 | B2 * | 1/2020 | Altschul ..... A61K 47/10 |
| 10,695,398 | B2 | 6/2020 | Van Der Meulen et al. |
| 10,702,508 | B2 | 7/2020 | Molina |
| 10,729,739 | B2 | 8/2020 | Olesen et al. |
| 10,799,488 | B2 | 10/2020 | Chen |
| 10,799,489 | B2 | 10/2020 | Chen |
| 10,849,888 | B2 | 12/2020 | Chen |
| 10,857,139 | B2 | 12/2020 | Jung et al. |
| 10,973,870 | B2 | 4/2021 | Olesen et al. |
| 11,116,775 | B2 * | 9/2021 | Altschul ..... A61K 31/337 |
| 11,160,796 | B2 | 11/2021 | Molina |
| 2002/0133833 | A1 | 9/2002 | Sawyers et al. |
| 2003/0225138 | A1 | 12/2003 | Sircar et al. |
| 2004/0009969 | A1 | 1/2004 | Jung et al. |
| 2004/0077605 | A1 | 4/2004 | Salvati et al. |
| 2004/0116417 | A1 | 6/2004 | Boubia et al. |
| 2005/0153968 | A1 | 7/2005 | Bi et al. |
| 2006/0025589 | A1 | 2/2006 | Binet et al. |
| 2006/0127902 | A1 | 6/2006 | Madden et al. |
| 2007/0004753 | A1 | 1/2007 | Sawyers et al. |
| 2007/0249697 | A1 | 10/2007 | Tachibana et al. |
| 2007/0254933 | A1 | 11/2007 | Jung et al. |
| 2008/0032935 | A1 | 2/2008 | Engel et al. |
| 2008/0139634 | A2 | 6/2008 | Jung et al. |
| 2009/0203622 | A1 | 8/2009 | Persson |
| 2009/0203623 | A1 | 8/2009 | Olesen et al. |
| 2009/0312295 | A1 | 12/2009 | McKearn et al. |
| 2010/0190991 | A1 | 7/2010 | Ouerfelli et al. |
| 2011/0003839 | A1 | 1/2011 | Jung et al. |
| 2012/0190718 | A1 | 7/2012 | Jung et al. |
| 2013/0029910 | A1 | 1/2013 | Meulen et al. |
| 2013/0045204 | A1 | 2/2013 | Andersen et al. |
| 2013/0072511 | A1 | 3/2013 | Jung et al. |
| 2013/0079241 | A1 | 3/2013 | Luo et al. |
| 2013/0116258 | A1 | 5/2013 | Smith et al. |
| 2013/0225821 | A1 | 8/2013 | Ouerfelli et al. |
| 2013/0253035 | A1 | 9/2013 | McDonnell et al. |
| 2014/0088129 | A1 | 3/2014 | Chen |
| 2014/0113870 | A1 | 4/2014 | Olesen et al. |
| 2014/0187641 | A1 * | 7/2014 | Dalton ..... C07D 295/088 514/655 |
| 2014/0199236 | A1 | 7/2014 | Chen et al. |
| 2014/0309262 | A1 | 10/2014 | Jung et al. |
| 2014/0314860 | A1 | 10/2014 | Shah et al. |
| 2014/0343111 | A1 | 11/2014 | Sawyers et al. |
| 2014/0349935 | A1 | 11/2014 | Persson |
| 2015/0133481 | A1 | 5/2015 | Dilhas et al. |
| 2016/0376252 | A1 | 12/2016 | Bonnefous et al. |
| 2017/0014399 | A1 | 1/2017 | Jung et al. |
| 2017/0035833 | A1 | 2/2017 | Van Der Meulen et al. |
| 2017/0290879 | A1 | 10/2017 | Olesen et al. |
| 2018/0318276 | A1 | 11/2018 | Jung et al. |
| 2018/0318277 | A1 | 11/2018 | Chen |
| 2019/0151335 | A1 * | 5/2019 | Altschul ..... A61K 47/26 |
| 2019/0167755 | A1 | 6/2019 | Persson |
| 2019/0269667 | A1 | 9/2019 | Chen |
| 2019/0269668 | A1 | 9/2019 | Chen |
| 2020/0237854 | A1 | 7/2020 | Olesen et al. |
| 2021/0121450 | A1 | 4/2021 | Jung et al. |
| 2021/0128673 | A1 | 5/2021 | Van Der Meulen et al. |
| 2021/0177821 | A1 * | 6/2021 | Chen ..... A61K 39/39558 |
| 2021/0361675 | A1 * | 11/2021 | Altschul ..... A61K 9/08 |
| 2022/0054468 | A9 * | 2/2022 | Molina ..... A61K 31/4166 |

FOREIGN PATENT DOCUMENTS

| | | | |
|---|---|---|---|
| AU | 2018206695 | C1 | 10/2020 |
| CN | 101032483 | | 9/2007 |
| CN | 101032483 | A | 9/2007 |
| CN | 101032486 | A | 9/2007 |
| CN | 101454002 | A | 6/2009 |
| CN | 101528308 | A | 9/2009 |
| CN | 101528309 | A | 9/2009 |
| CN | 102413831 | A | 4/2012 |
| CN | 104661658 | A | 5/2015 |
| CN | 104857157 | A | 8/2015 |
| DE | 2102605 | | 7/1971 |
| DE | 2614831 | | 10/1977 |
| DE | 2614831 | A1 | 10/1977 |
| EA | 030128 | | 6/2018 |
| EP | 0002259 | A2 | 6/1979 |
| EP | 0017976 | | 10/1980 |
| EP | 0017976 | A2 | 10/1980 |
| EP | 0002259 | | 10/1984 |
| EP | 0144098 | | 6/1985 |
| EP | 0144098 | A1 | 6/1985 |
| EP | 0331232 | | 9/1989 |
| EP | 0331232 | A2 | 9/1989 |
| EP | 0362179 | | 4/1990 |
| EP | 0362179 | A2 | 4/1990 |
| EP | 0494819 | | 1/1992 |
| EP | 0494819 | A1 | 7/1992 |
| EP | 0572191 | | 12/1993 |
| EP | 0572191 | A1 | 12/1993 |
| EP | 0578516 | | 1/1994 |
| EP | 0578516 | A1 | 1/1994 |
| EP | 0580459 | | 1/1994 |
| EP | 0580459 | A1 | 1/1994 |
| EP | 0721944 | A1 | 7/1996 |
| EP | 0770613 | | 5/1997 |
| EP | 0770613 | A1 | 5/1997 |
| EP | 0721944 | | 1/2001 |
| EP | 1632477 | | 3/2006 |
| EP | 1632477 | A1 | 3/2006 |
| EP | 1007080 | B1 | 4/2007 |
| EP | 1790640 | | 5/2007 |
| EP | 1790640 | A1 | 5/2007 |
| EP | 2439196 | A1 | 4/2012 |
| EP | 2900224 | A1 | 8/2015 |
| EP | 2945628 | A1 | 11/2015 |
| EP | 3305285 | A1 | 4/2018 |
| FR | 2693461 | | 1/1994 |

(56) References Cited

FOREIGN PATENT DOCUMENTS

| | | | |
|---|---|---|---|
| FR | 2693461 | A1 | 1/1994 |
| FR | 2715402 | | 7/1995 |
| FR | 2715402 | A1 | 7/1995 |
| FR | 2845384 | | 4/2004 |
| FR | 2845385 | A1 | 4/2004 |
| GB | 0800244 | A | 8/1958 |
| HK | 1212221 | A1 | 6/2016 |
| HU | 217893 | | 5/2000 |
| ID | 2016/03647 | | 5/2016 |
| JP | 59-210083 | A | 11/1984 |
| JP | 59210083 | | 11/1984 |
| JP | 60-239737 | A | 11/1985 |
| JP | 64-009978 | A | 1/1989 |
| JP | 1009978 | | 1/1989 |
| JP | 02-019363 | A | 1/1990 |
| JP | 0219363 | | 1/1990 |
| JP | 08-009997 | | 1/1996 |
| JP | 10-009978 | A | 1/1998 |
| JP | 2845384 | B2 | 1/1999 |
| JP | 2003-530348 | | 10/2003 |
| JP | 2845384 | A1 | 4/2004 |
| JP | 2004-525175 | | 8/2004 |
| JP | 2004-252175 | A | 9/2004 |
| JP | 2006-022118 | A | 1/2006 |
| JP | 2006-510600 | | 3/2006 |
| JP | 2006-265244 | A | 10/2006 |
| JP | 2008-512419 | A | 4/2008 |
| JP | 2008-099977 | A | 5/2008 |
| JP | 2008-540523 | | 11/2008 |
| JP | 2009-531439 | | 9/2009 |
| JP | 2010-500975 | A | 1/2010 |
| JP | 2010-504307 | A | 2/2010 |
| JP | 2011-503075 | A | 1/2011 |
| JP | 2011-068653 | A | 4/2011 |
| JP | 2012-211190 | A | 11/2012 |
| JP | 2012-236843 | A | 12/2012 |
| JP | 5133975 | B2 | 1/2013 |
| JP | 2015-531373 | A | 11/2015 |
| JP | 2015-534582 | A | 12/2015 |
| JP | 2016-508991 | A | 3/2016 |
| JP | 6351597 | B2 | 7/2018 |
| JP | 2018-150365 | A | 9/2018 |
| NZ | 705815 | A | 8/2018 |
| UA | 117663 | | 9/2018 |
| WO | 90/13646 | A1 | 11/1990 |
| WO | WO 90/13646 | | 11/1990 |
| WO | 97/00071 | A1 | 1/1997 |
| WO | WO 97/00071 | | 1/1997 |
| WO | 97/13646 | A1 | 4/1997 |
| WO | 97/19064 | A1 | 5/1997 |
| WO | WO 97/19064 | | 5/1997 |
| WO | 97/19931 | A1 | 6/1997 |
| WO | WO 97/19931 | | 6/1997 |
| WO | 00/17163 | A1 | 3/2000 |
| WO | WO 00/17163 | | 3/2000 |
| WO | 00/26195 | A1 | 5/2000 |
| WO | WO 00/026195 | | 5/2000 |
| WO | 00/44731 | A1 | 8/2000 |
| WO | WO 00/044731 | | 8/2000 |
| WO | 01/07048 | A1 | 2/2001 |
| WO | WO 01/007048 | | 2/2001 |
| WO | 01/92253 | A2 | 12/2001 |
| WO | 01/94346 | A1 | 12/2001 |
| WO | WO 01/092252 | | 12/2001 |
| WO | WO 01/094346 | | 12/2001 |
| WO | 02/53155 | A1 | 7/2002 |
| WO | WO 02/053155 | | 7/2002 |
| WO | 02/81453 | A1 | 10/2002 |
| WO | WO 02/081453 | | 10/2002 |
| WO | 03/29245 | A1 | 4/2003 |
| WO | 03/32994 | A2 | 4/2003 |
| WO | WO 03/029245 | | 4/2003 |
| WO | WO 03/032994 | | 4/2003 |
| WO | 03/57220 | A1 | 7/2003 |
| WO | WO 03/057220 | | 7/2003 |
| WO | WO 03/093243 | | 11/2003 |
| WO | WO 03/096980 | | 11/2003 |
| WO | 2004/022572 | A1 | 3/2004 |
| WO | WO 2004/022572 | | 3/2004 |
| WO | 2004/031160 | A2 | 4/2004 |
| WO | WO 2004/030633 | A2 | 4/2004 |
| WO | WO 2004/031160 | | 4/2004 |
| WO | 2004/070050 | A2 | 8/2004 |
| WO | WO 2004/070050 | | 8/2004 |
| WO | 2004/111031 | A1 | 12/2004 |
| WO | WO 2004/111031 | | 12/2004 |
| WO | 2005/042488 | A1 | 5/2005 |
| WO | WO 2005/042488 | | 5/2005 |
| WO | 2005/059109 | A2 | 6/2005 |
| WO | WO 2005/059109 | | 6/2005 |
| WO | 2005/060661 | A2 | 7/2005 |
| WO | WO 2005/060661 | | 7/2005 |
| WO | 2005/089752 | A2 | 9/2005 |
| WO | WO 2005/089752 | | 9/2005 |
| WO | 2005/099693 | A2 | 10/2005 |
| WO | WO 2005/099693 | | 10/2005 |
| WO | 2006/010641 | A2 | 2/2006 |
| WO | 2006/010642 | A1 | 2/2006 |
| WO | WO 2006/010642 | | 2/2006 |
| WO | 2006/027266 | A1 | 3/2006 |
| WO | 2006/028226 | A1 | 3/2006 |
| WO | WO 2006/028226 | | 3/2006 |
| WO | 2006/124118 | A1 | 11/2006 |
| WO | WO 2006/124118 | | 11/2006 |
| WO | WO 2007/012661 | A1 | 2/2007 |
| WO | 2007/045877 | A1 | 4/2007 |
| WO | WO 2007/045877 | | 4/2007 |
| WO | 2007/126765 | A2 | 11/2007 |
| WO | 2007/127010 | A2 | 11/2007 |
| WO | WO 2007/126765 | | 11/2007 |
| WO | WO 2007/127010 | | 11/2007 |
| WO | 2008/034909 | A2 | 3/2008 |
| WO | 2008/119015 | A2 | 10/2008 |
| WO | WO 2008/119015 | | 10/2008 |
| WO | 2009/055053 | A2 | 4/2009 |
| WO | WO 2009/055053 | | 4/2009 |
| WO | 2009/061587 | A1 | 5/2009 |
| WO | 2009/101530 | A1 | 8/2009 |
| WO | 2010/099238 | A1 | 9/2010 |
| WO | WO 2010/099238 | | 9/2010 |
| WO | WO 2011/103202 | A2 | 8/2011 |
| WO | 2011/106570 | A1 | 9/2011 |
| WO | WO 2011/106570 | | 9/2011 |
| WO | WO 2012/018948 | A2 | 2/2012 |
| WO | WO 2012/142208 | A1 | 10/2012 |
| WO | WO 2012/145330 | A1 | 10/2012 |
| WO | 2012/158884 | A1 | 11/2012 |
| WO | WO 2012/158884 | | 11/2012 |
| WO | WO 2013/066440 | A1 | 5/2013 |
| WO | 2013/079964 | A1 | 6/2013 |
| WO | WO 2013/079964 | | 6/2013 |
| WO | 2013/153342 | A1 | 10/2013 |
| WO | WO 2013/152342 | A1 | 10/2013 |
| WO | WO 2013/184681 | A1 | 12/2013 |
| WO | WO 2014/052237 | A1 | 4/2014 |
| WO | 2014/113260 | A1 | 7/2014 |

OTHER PUBLICATIONS

U.S. Appl. No. 14/151,106, filed Jan. 9, 2014, Chen et al.

US. Appl. Jan. 9, 2014, Chen et al., U.S. Appl. No. 14/151,106.

Wolf, et al., Molecular Endocrinology, Transcriptional Regulation of Prostate Kallikrein-Like Genes by Androgen, 1992, vol. 6, No. 5, pp. 753-762.

Yoshino et al., Design and synthesis of an androgen receptor pure antagonist (CH5137291) for the treatment of castration-resistant prostate cancer. Bioorg Med Chem. Dec. 1, 2010;18(23):8150-7. doi: 10.1016/j.bmc.2010.10.023. Epub Oct. 15, 2010.

Abstract submitted by Samedy Ouk, Prostate Cancer Foundation Scientific Retreat, Scottsdale, Arizona, Sep. 29-Oct. 1, 2005.

American Urological Association—Castration-Resistant Prostate Cancer—https://www.auanet.org/education/guidelines/castration-resistant-prostate-cancer.cfm.

(56) References Cited

OTHER PUBLICATIONS

Bhupinder Singh et al. "Self-Emulsifying Drug Delivery Systems (SEDDS): Formulation Development, Characterization, and Applications "Critical Reviews"" in Therapeutic Drug Carrier Systems, 26 (5), 427-521 (2009).
Carver et al., "Reciprocal Feedback Regulation of P13K and Androgen Receptor Signaling in PTEN-Deficient Prostate Cancer", Cancer Cell., 2011, 19, 575-586.
Chen et al., Molecular determinants of resistance to antiandrogen therapy. Nat Med. Jan. 2004; 10(1):33-9. Epub Dec. 21, 2003.
Cousty-Berlin, et al., "Preliminary Pharmacokinetics and Metabolism of Novel Non-steroidal Antiandrogens in the Rat: Relation of their Systemic Activity to the Formation of a Common Metabolite," J. Steroid Biochem. Malec. Biol., vol. 51, No. 1/2, pp. 47-55 (1994).
Depalo et al., "GnRH agonist versus GnRH antagonist in in vitro fertilization and embryo transfer (IVF/ET)", Reproductive Biology and Endocrinology, 2012, 10, 26-33.
Design of Prodrugs, edited by H. Bundgaard, (Elsevier, 1985).
Dorwald, F. Zaragoza. Side Reactions in Organic Synthesis: A Guide to Successful Synthesis Design, Weinheim: WILEY-VCH Verlag GmbH & Co. KGaA, 2005, Preface.
FDA ODAC Briefing Document; "Issues Concerning the Development of Products for the Treatment of Patients with Non-Metastatic Castration-Resistant Prostate Cancer"; Sep. 4, 2011; 9 pages.
Fizazi et al., "Activity and safety of ODM-201 in patients with progressive metastatic castration-resistant prostate cancer (ARADES): an open-label phase 1 dose-escalation and randomized phase 2 dose expansion trial", Lancet Oncology, vol. 15, No. 9, pp. 975-985 (2014).
Foks et al., "Synthesis, Fungicidal and Antibacterial Activity of New Pyridazine Derivatives", Heterocycles, 2009, 78(4), 961-975.
Xu Guan Yu et al., "Chinese Prescription Drugs", vol. 10, No. 4, New drugs will change the current status of prostate cancer treatment, pp. 28-30.
Heath Elisabeth 1 et al: A phase 1 dose-escalation study of oral BR-DIM (BioResponse 3,3 -Diindolylmethane) in castrate-resistant, non-metastatic prostate cancer, American Journal of Translational Research, vol. 2, No. 4, 2010, pp. 402-411.
Huang, Z.Q., Li, J. & Wong, J. AR possess an intrinsic hormone-independent transcriptional activity. Mol Endocrinol 16, 924-37 (2002).
Jordan, V. C. Nature Reviews: Drug Discovery, 2, 2003, 205.
Karp et al., "Prostate Cancer Prevention: Investigational Approaches and Opportunities", Cancer Res., v. 56 (Dec. 15, 1996) pp. 5547-5556.
Lu et al. "Molecular Mechanisms of Androgen-Independent Growth of Human Prostate Cancer LNCaP-AI Cells", Endocrinology 1999, vol. 140, No. 11, pp. 5054-5059.
Manolagas et al., "Sex Steroids and Bone", Recent Prog Harm Res, 2002, 57, 385-409.
"A Phase 1 Study of MDV3100 in Patients With Castration-Resistant (Hormone-Refractory) Prostate Cancer," NCT00510718, Apr. 14, 2009 (v8).
"A Phase 1 Study of MDV3100 in Patients With Castration-Resistant (Hormone-Refractory) Prostate Cancer," NCT00510718, Jul. 31, 2007 (v1).
"A Study of Apalutamide (ARN-509) in Men With Non-Metastatic Castration-Resistant Prostate Cancer (SPARTAN)," ClinicalTrials.gov Identifier: NCT01946204, 2021, pp. 1-8.
"IMAAGEN : Impact of Abiraterone Acetate in Prostate-Specific Antigen History of Changes for Study NCT01314118," Clinical Trials.gov, Sep. 11, 2012 (V18), pp. 1-7.
"Medivation and Astellas Complete Enrollment in Phase 3 Affirm Trial of MDV3100 in Advanced Prostate Cancer;—Clinical development of MDV3100 also initiated in Japan—," LexisNexis, 2010, pp. 1-3.
"Medivation Announces Initiation of Phase 3 Clinical Trial of MDV3100 in Advanced Prostate Cancer," LexisNexis, 2009, pp. 1-3.
"Medivation Announces Positive New Efficacy Data From Phase 1-2 Trial of MDV3100 in Advanced Prostate Cancer Patients," LexisNexis, 2009, pp. 1-3.
"Medivation Reports Second Quarter Financial Results and Provides Corporate Update," Conference Call Today at 4.30pm Eastern Time, Marketwire, Aug. 9, 2012.
"Positive data on Antisoma's ASA404 presented at ASCO," Retrieved at Small Molecules, Retrieved on Jun. 2, 2008, pp. 1-3.
Ahmed M, et al., "Adaptation and clonal selection models of castration-resistant prostate cancer: Current perspective," International Journal of Urology, vol. 20, 2013, pp. 362-371.
Bono J S D. et al., "Prednisone plus cabazitaxel or mitoxantrone for metastatic castration-resistant prostate cancer progressing after docetaxel treatment: a randomised open-label trial," Lancet, vol. 376, 2010, pp. 1147-1154.
Cougar Biotechnology, Cougar Biotechnology presents positive CB7630 Clinical Data at AACR Annual Meeting Late-Breaking Clinical Trials Session, Cougar Biotechnology, Apr. 17, 2007.
Danila D. C. et al., "Abiraterone acetate and prednisone in patients (Pts) with progressive metastatic castration resistant prostate cancer (CRPC) after failure of docetaxel-based chemotherapy," Journal of Clinical Oncology, vol. 26, Issue 15, 2008, pp. 5019.
De Bono et al., "Anti-tumor activity of abiraterone acetate (AA), a CYP17 inhibitor of androgen synthesis, in chemotherapy naive and docetaxel pre-treated castration resistant prostate cancer (CRPC)," J. Clin. OncoL (Meeting abstracts),. vol. 26 (May 20 Supplement), abstract No. 5005 (2008).
Eisenberger M A. et al., "Comparison of two doses of cabazitaxel plus prednisone in patients (pts) with metastatic castration-resistant prostate cancer (mCRPC) previously treated with a docetaxel (D)—containing regimen," Journal of Clinical Oncology, vol. 30, Issue 15, 2012.
Form 10-Q filed with the United States Securities and Exchange Commission by Medivation, Inc. for the quarterly period that ended on Jun. 30, 2012.
Hoimes C J. et al., "Redefining hormone resistance in prostate cancer," Ther Adv Med Oncol, vol. 2, Issue 2, 2010, pp. 107-123.
Lara P N. et al., Randomized Phase III Placebo-Controlled Trial of Carboplatin and Paclitaxel With or Without the Vascular Disrupting Agent Vadimezan (ASA404) in Advanced Non-Small-Cell Lung Cancer, Journal of Clinical Oncology, vol. 29, Issue 22, Aug. 2011, pp. 2965-2971.
Logothetis C. J et al., "Identification of an androgen withdrawal responsive phenotype in castrate resistant prostate cancer (CRPC) patients (pts) treated with abiraterone acetate (AA)," Journal of Clinical Oncology, vol. 26, Issue 15, 2008, pp. 5017-5017.
LoRusso P M. et al., "Clinical Development of Vascular Disrupting Agents: What Lessons Can We Learn From ASA404?,"Journal of Clinical Oncology, 2011, pp. 2952-2955.
Medivation Reports First Quarter 2010 Financial Results and Provides Corporate Update;—Conference Call Today at 4:30 p.m. Eastern Time, 2010, pp. 1-6.
Mohler J. et al., "Prostate Cancer Clinical Practice Guidelines in Oncology," National Comprehensive Cancer Network, vol. 8, Issue 2, Feb. 2010, pp. 162-200.
Mohler. J. L. et al., "Prostate Cancer, Version 3.2012 featured updates to the NCCN Guidelines," Official Journal of the National Comprehensive Cancer Network, vol. 10, Issue 9, 2012.
Opposition—Statement of Grounds and Particulars received for Australian Patent Application No. 2018206695 mailed on Apr. 30, 2021, 12 pages.
Oudard S. et al., "Cabazitaxel Versus Docetaxel As First-Line Therapy for Patients With Metastatic Castration-Resistant Prostate Cancer: A Randomized Phase III Trial—FIRSTANA," Journal of Clinical Oncology, vol. 35, Issue 28, 2017, pp. 3189-3197.
Oudard S. et al., "First-line use of cabazitaxel in chemotherapy-naive patients with metastatic castrationresistant prostate cancer (mCRPC): A three-arm study in comparison with docetaxel," Journal of Clinical Oncology, vol. 30, Issue 15, 2012.
Parente P. et al., "Emerging and second line therapies for the management of metastatic castration-resistant prostate cancer: The Australian perspective," Asia-Pacific Journal of Clinical Oncology, vol. 8, 2012, p. 31-42.

(56) References Cited

OTHER PUBLICATIONS

Parker C. et al., "Updated analysis of the phase III, double-blind, randomized, multinational study of radium-223 chloride in castration-resistant prostate cancer (CRPC) patients with bone metastases (ALSYMPCA)," Journal of Clinical Oncology, vol. 30, Issue 18, 2012.
Pili R. et al., "Phase II Study on the Addition of ASA404 (Vadimezan; 5,6- Dimethyixanthenone-4-Acetic Acid) to Docetaxel in CRMPC," Clin Cancer Res, vol. 16, Issue 10, 2010, pp. 2906-2914.
Ryan C. et al., "Impact of prior ketoconazole therapy on response proportion to abiraterone acetate, a 17-alpha hydroxylase C17,20-lyase inhibitor in castration resistant prostate cancer (CRPC)," Journal of Clinical Oncology, vol. 26, Issue 15, 2008, pp. 5018.
Ryan et al.., "Prostate Specific Antigen Only Androgen Independent Prostate Cancer: Natural History, Challenges in Management and Clinical Trial Design." J, Urology, vol. 178:S25-S29 (2007).
Ryan, et al., "Phase I Clinical Trial of the CYP17 Inhibitor Abiraterone Acetate Demonstrating Clinical Activity in Patients With Castration-Resistant Prostate Cancer Who Received Prior Ketoconazole Therapy",JANSSEN EXHIBIT 2133, *Wockhardt* vs. *Janssen*, Case # IPR2016-01582, Journal of Clinical Oncology vol. 28, No. 9. Mar. 20, 2010 pp. 1481-1488.
Sartor O. et al., "Advanced Prostate Cancer 2010: What a Year!," Clinical Genitourinary Cancer, vol. 8, Issue 1, 2010, pp. 8-9.
Sheikh N A. et al., "Sipuleucel-T immune parameters correlate with survival: an analysis of the randomized phase 3 clinical trials in men with castration-resistant prostate cancer," Cancer Immunol Immunother, vol. 62, 2013, pp. 137-147.
Small E.J. et al., "Prostate Cancer: Evolution or Revolution," Journal of Clinical Oncology, vol. 29, Issue 27, 2011, pp. 3595-3598.
Smith M R. et al., "Disease and Host Characteristics as Predictors of Time to First Bone Metastasis and Death in Men With Progressive Castration—Resistant Nonmetastatic Prostate Cancer," Cancer, 2011, pp. 2077-2085.
Smith M R. et al., "Natural History of Rising Serum Prostate-Specific Antigen in Men With Castrate Nonmetastatic Prostate Cancer," Journal of Clinical Oncology, vol. 23, Issue 13, May 2005, pp. 2918-2925.
Smith M. et al., "Denosumab and bone-metastasis-free survival in men with castration-resistant prostate cancer: results of a phase 3, randomised, placebo-controlled trial," Lancet, vol. 379, 2012, pp. 39-46.
Taylor R A. et al., "Stem cells in prostate cancer: treating the root of the problem," Endocrine-Related Cancer, vol. 17, 2010, pp. R273-R285.
A Textbook of Drug Design and Development, P. Krogsgaard-Larson and H. Bundgaard, eds. Ch 5, pp. 113-191 (Harwood Academic Publishers, 1991).
Al-Salama Zaina T: "Apalutamide: First Global Approval", Drugs, Adis International LTD, NZ, vol. 78, No. 6, Mar. 31, 2018 (Mar. 31, 2018), pp. 699-705, ISSN: 1179-1950, DOI: 10.1007/S40265-018-0900-Z.
Antonarakis, Eur Urol Rev., Management of metastatic castration-resistant prostate cancer, 2011 ; 6(2): 90-96.
Auricchio et al. (European Oncology & Haematology, 2012, vol. 8, No. 1, pp. 32-35).
Balbas Minna D et al: "Overcoming mutation-based resistance to antiandrogens with rational drug design", E-LIFE, vol. 2, pp. e00499/1-21, XP009173001.
Bredenberg, S. et al. (Jan. 1, 2003). "New Concepts in Administration of Drugs in Tablet Form," Comprehensive Summaries of Uppsala Dissertations from the Faculty of Pharmacy ACTA Universitatis Upsaliensis Uppsala, 83 pages.
Castration-Resistant Prostrate Cancer, American Urological Association, www.auanet.org/education/guidelines/castration-resistant-prostate-cancer - cfm, 2015, 21 pages.
Clegg et al., "ARN-509: A Novel Antiandrogen for Prostate Cancer Treatment", Cancer Research, Mar. 15, 2012, 72(6), 1494-1503.
Elokdah et al., "Design, Synthesis, and Biological Evaluation of Thia-Containing Compounds with Serum HDL-Cholesterol-Elevating Properties", J. Med. Chem., 2004, 47(3), 681-695.
FDA: "FDA approves new treatment for a certain type of prostate cancer using novel clinical trial endpoint", Feb. 14, 2018 (Feb. 14, 2018), Retrieved from the Internet: URL:https://www.fda.gov/newsevents/newsroom/pressannouncements/ucm596768.htm [retrieved on Jul. 12, 2018]; XP-002783009; 4 pages.
Fu, et al., Biochim Biophys Acta., Progress of molecular targeted therapies for prostate cancers, 2012; 1825(2): 140-152; 27 pages.
Geynisman Daniel M et al: "Second-generation Androgen Receptor-targeted Therapies in Nonmetastatic Castration-resistant Prostate Cancer: Effective Early Intervention or Intervening Too Early?", European Urology, Elsevier, Amsterdam, NL, vol. 70, No. 6, May 26, 2016 (May 26, 2016), pp. 971-973, ISSN: 0302-2838, DOI:10.1016/J.EURUR0.2016.05.026.
Hou, et al., Hindawi Publishing Corpration, Advances in Urology, Redefining Hormone Sensitive Disease in Advanced Prostate Cancer, vol. 2012, Article ID ID 978531, 6 pages.
Janssen Pharmaceutical Companies: "ERLEADA safety and efficacy". See full prescribing information for ERLEADA., Retrieved from the Internet: URL:https://www.accessdata.fda.gov/drugsatfda _ docs/label/2018/21 0951 s000lbl.pdf, [retrieved on Feb. 5, 2020].
Janssen: "Submits New Drug Application to U.S. FDA for Apalutamide (ARN-509) to Treat Men with Non-Metastatic Castration-Resistant Prostate Cancer", Oct. 11, 2017 (Oct. 11, 2017) Retrieved from the Internet: URL:https://www.prnewswire.com/news-releases/janssen-submits-new-drug-application-to-usfda-for-apalutamide-arn-509-to-treat-men-with-non-metastatic-castration-resistant-prostatecancer-300534 704. html [retrieved on Jul. 12, 2018].
Kim, et al., Korean Journal of Urology, Current Treatment Strategies for Castration-Resistant Prostate Cancer, 2011, pp. 157-165.
Liu Et Al: "Lineage relationship between LNCaP and LNCaP-derived prostate cancer cell lines", PROSTATE., vol. 60, No. 2, Jan. 1, 2004 (Jan. 1, 2004), pp. 98-108.
Lonergan, et al., Journal of Carcinogenesis, Androgen receptor signaling in prostate cancer development and progression, 2011, 19 pages.
Molina et al., Phase I study of apalutamide (ARN) plus abiraterone acetate (AA), docetaxel (D) in patients (pts) with metastatic castrate-resistant prostate cancer (mCRPC), Annals of Oncology, vol. 28, Supplement 5, Abstract No. 837TiP, Sep. 2017.
Penson et al: "Enzalutamide Versus Bicalutamide in Castration-Resistant Prostate Cancer: The STRIVE Trial",Journal Of Clinical Oncology, vol. 34, No. 18, Jun. 20, 2016 (Jun. 20, 2016), pp. 2098-2106, US, ISSN: 0732-183X, DOI: 10.1200/JC0.2015.64.9285.
Rathkopf D E (Correspondence) et al.: "A first-in-human, open-label, phase 1/11 safety, pharmacokinetic, and proof-of-concept study of ARN-509 in patients with progressive advanced castration-resistant prostate cancer (CRPC )", Journal of Clinical Oncology; ASCO Annual Meeting 2011, American Society of Clinical Oncology, US; Chicago, IL, United States, vol. 29, No. 15, Suppl. 1, May 20, 2011 (May 20, 2011), p. TPS190.
Rathkopf Dana E (Correspondence) et al: "Phase I/II safety and pharmacokinetic (PK) study of ARN-509 in patients with metastatic castration-resistant prostate cancer (mCRPC): Phase I results of a Prostate Cancer Clinical Trials Consortium study", Journal of Clinical Oncology, American Society of Clinical Oncology, US vol. 30, No. 5, Suppl. 1 Feb. 10, 2012 (Feb. 10, 2012).
Rathkopf Dana E et al: "Phase I study of ARN-509, a novel antiandrogen, in the treatment of castration-resistant prostate cancer", J Clin ONC,vol. 31 (28), Oct. 1, 2013, pp. 3525-3530, XP008166079.
Rathkopf, et al., "A phase I study of the androgen signaling inhibitor ARN-509 in patients with metastatic castration Resistant prostate cancer (mCRPC)" Journal of Clinical Oncology (2012), vol. 30. suppl. 1.
Riegman, et al., Molecular Endocrinology, The Promoter of the Prostate-Specific Antigen Gene Contains a Functional Androgen Responsive Element, 1991, pp. 1921-1930.

(56) References Cited

OTHER PUBLICATIONS

Scott, et al: Abiraterone Acetate: A Guide to Its Use in Metastatic Castration-Resistant Prostate Cancer; ADIS Drug Clinical; Drugs and Aging, 2012, vol. 29, vol. 3, 243-248.
Shang, Y., Myers, M. & Brown, M. Formation of the androgen receptor transcription complex. Mol Cell 9, 601-10 (2002).
Sharifi et al., Advanced Drug Delivery Reviews, vol. 28, No. 1, 1997, pp. 121-138.
Shore et al.: "Novel Antiandrogen ARN-509 in High-Risk Nonmetastatic CastrationResistant Prostate Cancer", The Journal of Urology, vol. 193, No. 4S, May 19, 2015 (May 19, 2015).
Shore: "Darolutamide (ODM-201) for the treatment of prostate cancer", Expert Opinion On Pharmacotherapy, vol. 18, No. 9, Jun. 13, 2017 (Jun. 13, 2017), pp. 945-952, London, UK, ISSN: 1465-6566, DOI: 10.1080/14656566.2017.1329820.
Simone, "Oncology: Introduction", Cecil Textbook of Medicine, 20th Edition, vol. 1, 1996, 1004-1010.
Smith Matthew R et al: "Phase 2 Study of the Safety and Antitumor Activity of Apalutamide (ARN-509), a Potent Androgen Receptor Antagonist, in the High-risk Non metastatic Castrationresistant Prostate Cancer Cohort", European Urology, Elsevier, Amsterdam, NL, vol. 70, No. 6, May 6, 2016 (May 6, 2016), pp. 963-970, ISSN: 0302-2838, DOI: 10.1016/J.EURUR0.2016.04.023.
Matias et al., "Structural Basis for the Glucocorticoid Response in a Mutant Human Androgen Receptor (AR(ccr)) Derived from an Androgen-Independent Prostate Cancer", J Med Chern, 2002, 45, 1439-1446.
Muller et al., "BCR First Exon Sequences Specifically Activate the BCRIABL Tyrosine Kinase Oncogene of Philadelphia ChromosomePositive Fluman Leukemias", Mol. & Cell, Biol., 1991, 11(4), 1785-1792.
Nam et al., Action of the Src Family Kinase Inhibitor, Dasatinib (BMS-354825), on Human Prostate Cancer Celle, Cancer Res., 2005, v. 65(20), pp. 9185-9189.
Nathan Lawrentschuk et al: 11 Efficacy of a Second Line Luteinizing Hormone-Releasing Hormone Agonist After Advanced Prostate Cancer Biochemical Recurrence 11 , Journal of Urology, vol. 185, No. 3, Mar. 2011 (2011-03), pp. 848-854, XP028358931.
NCBI, "Definition: Homo sapiens Androgen", Nucleotide, 2007, 7 pages NM.sub.-000044<http://www.ncbi.nlm.nih.gov:80/entrez/viewer.fcgi?cmd=- Retrieve&db=nucleotide&list.sub.- uids= 21322251 &dopt=Gen Ban k&term=sapiens+AR+androgen+receptor+prostate+cancer&qty= 1>gi:21322251.
NM.sub.—000044<http://www.ncbi.nlm.nih.gov:80/entrez/viewer.fcgi?cmd=R-etrieve&db=nucleotide&list.sub.-uids=21322251&dopt=GenBank&term=sapiens+A-R+androgen+receptor+prostate+cancer&qty=1>gi:21322251, printed Oct. 24, 2007.
Raffo et al. Overexpression of bcl-2 Protects Prostate Cancer Cells from Apoptosis in Vitro and Confers Resistance to Androgen Depletion in Vivo. Cancer Research. 1995. v. 55.4438-4445.
Rampurna Prasad Gullapalli: "Soft gelatin capsules (softgels)", Journal of Pharmaceutical Sciences, vol. 99, No. 10, Oct. 18, 2010 (Oct. 18, 2010), pp. 4107-4148, XP055090285.
Sambrook et al., "Molecular Cloning: A Laboratory Manual", 2.sup.nd Edition, Table of Contents, Cold Spring Harbor Laboratory Press, Cold Spring Harbor, 1989, 30 pages.
The Pharmacological Basis of Therapeutics, Goodman and Gilman, eds., Macmillan Publishing Co., New York, 1941.
The Practice of Medicinal Chemistry, Camille G. Wermuth et al., Ch 31, (Academic Press, 1996).
Vogelzang, Nicholas, et al: Goserlin Versus Orchiectomy in the Treatment of Advanced Prostate Cancer: Final Results of a Randomized Trial; Urology, 46 (2), 1995, 220-226.
Zheng, Q. et al. (2000). "Synthesis and Nonlinear Optical Properties of p-(Dimethylamino) benzylidene Dyes Containing Different Acceptors," Chemistry Letters 29(12): 1426-1427.
Farmacopea Argentina, seventh edition, Decreto 202, Buenos Aires, Jun. 12, 2003 p. 15.
Rathkopf D E (Cousespondence) et al., "A first-in human, open-label, phase I/II safety, pharmacokinetic, and proof-of-concept study of ARN-509 in patients with progressive advanced castration-resistant prostate cancer (CRPC )", Journal of Clinical Oncology; ASCO Annual Meeting 2011, American Society of Clinical Oncology, US; Chicago, IL, United States, (20110520), vol. 29, No. 15, Suppl. 1, ISSN 0732-183X, p. TPS190, XP008166220.
Tenuta, et al., "Clinical trial risk in castration-resistant prostate cancer: immunotherapies show promise", BJU Int 2014; 113; E82-E89.
"Endpoints in asthma drug trials—what do they means?" Drug and Therapeutics Bulletin vol. 6, vol. 44, No. 3, 2006, vol. 44, No. 3, pp. 21.
Akaza et al., "Combined Androgen Blockade With Bicalutan1ide for Advanced Prostate Cancer", Cancer, 2009, pp. 3437-3445.
Amm et al., "Metastatic Castration-Resistant Prostate Cancer: Critical Review of Enzalutamide", Clinical Medicine Insights: Oncology, vol. 7, 2013, pp. 235-245.
AUA 2018, "Results from Spartan: PSA Outcomes in Patients with Nonmetastatic Castration-Resistant Prostate Cancer Treated with Apalutamide".
BIO Industry Analysis: Clinical Development Succes Rates 2006-2015.
Casodex (Registered) 1995 FDA review pp. 26, 43 and 49, accessed via https ://www. accessdata. fda. gov /drug satfda _ docs/nda/pre96/020498Orig1 s000rev.pdf.
Casodex (Registered) 2008 FDA label.
Clegg et al., "ARN-509: A Novel Antiandrogen for Prostate Cancer Treatment", Cancer Res; vol. 72, No. 6, Mar. 15, 2012, pp. 1494-1503.
Clinical study protocol for NCT00510718, archive version vol. 9, No. 3, Apr. 2012.
Clinical study protocol for NCT00974311, archive version, Jul. 10, 2012.
Clinical study protocol for NCT01171898, archive version 5 Mar. 22, 2012.
Clinical study protocol for NCT01212991, archive version 34, Jun. 11, 2012.
Clinical study protocol for NCT01288911, archive version 18, Aug. 24, 2012.
Clinical study protocol for NCT01317641, archive version 4 Aug. 6, 2012.
Clinical study protocol for NCT01337518, archive version 1 Apr. 18, 2012.
Clinical study protocol for NCT01664923, archive version 2 Aug. 30, 2012.
ClinicalTrials.gov search results for the term "apalutamide", first posted until Sep. 22, 2013.
Courtney et al., "The evolving paradigm of second-line hormonal therapy options for castration-resistant prostate cancer", Curr. Opin. Oneal., vol. 24, No. 3, May 2012, pp. 272-277.
Excerpt from "ESMO 2012 late-breaking, press and deferred publication abstracts", Annals of Oncology, Abstract Book of the 37th ESMO Congress, vol. 23, No. Suppl. 9, Sep. 17, 2012, p. ixe1.
Excerpt from clinicaltrials.gov: clinical study NCT0 1790126, as it was available on Sep. 12, 2013.
Excerpt from clinicaltrials.gov: clinical study NCT01547299, as it was available on Jul. 9, 2012.
Excerpt from the USPTO's assignment-register 502648248 of Jan. 23, 2014.
FDA-label for CASODEX 9 (Registered) (bicalutamide) of Nov. 2009.
FDA-label for EULEXIN® (flutamide) of Jun. 2001.
FDA-label for NOVANTRONE (Registered), (mitoxantrone) of Aug. 2008.
FDA-label for XTANDI (Registered) (enzalutamide) of Aug. 2012.
Goa L.K., Bicalutamide in advanced prostate cancer. A review, Drugs aging, vol. 12, May 1998, pp. 401-422.
Golshayan et al., "Enzalutamide: an evidence-based review of its use in the treatment of prostate cancer", Core Evidence, vol. 8, 2013, pp. 27-35.
Gomella, "Effective Testosterone Suppression for Prostate Cancer: Is There a Best Castration Therapy?", Reviews in Urology, vol. 11, No. 2, 2009, pp. 52-60.

(56) References Cited

OTHER PUBLICATIONS

Harrison et al., "Gonadotropin-releasing hormone and its receptor in normal and malignant cells", Endocrine-Related Cancer, vol. 11, 2004, pp. 725-748.
Heidenreich, "Guidelines and Counselling for Treatment Options in the Management of Prostate Cancer in Prostate Cancer"Springer, Berlin Heidelberg, 2007, pp. 131-162.
Jones et al., "Re: Acceptance and Durability of Surveillance as a Management Choice in Men with Screen-Detected, Low-Risk Prostate Cancer: Improved Outcomes with Stringent Enrollment Criteria", European Urology, vol. 59, 2011, pp. 1066-1070.
Leibowitz et al., "Targeting the androgen receptor in the management of castration-resistant prostate cancer: rationale progress, and future directions", Curr. Oncol., vol. 19, 2012, pp. S22-S31.
Mccutcheon, "Enzalutamide: A New Agent for the Prostate Cancer Treatment Armamentarium", Journal of the Advanced Practitioner in Oncology, vol. 4, No. 3, May 2013, pp. 182-185.
Menon et al., "Enzalutamide, a Second Generation Androgen Receptor Antagonist: Development and Clinical Applications in Prostate Cancer", Curr. Oneal. Rep., vol. 15, 2013, pp. 69-75.
Overview on clinical study NCT01171897 of Mar. 22, 2012, accessible via: https://clinicaltrials.gov/ct2/history/NCT01171898?V _5-View#StudyPageTop.
Rathkopf et al., "A phase II study of the androgen signaling inhibitor ARN-509 in patients with castration-resistant prostate cancer (CRPC)", Journal of Clinical Oncology, Abstract book of the 2012 ASCO Annual Meeting Chicago, USA, vol. 30, issue 15 supplement May 12, 2012, TPS4697.
Ryan et al., "Androgen Receptor Rediscovered: The New Biology and Targeting the Androgen Receptor Therapeutically", Journal of Clinical Oncology, vol. 29, No. 27, Sep. 20, 2011, pp. 3651-3658.
Sadar, "Advances in small molecule inhibitors of androgen receptor for the treatment of advanced prostate cancer", World J. Urology, vol. 30, 2012, pp. 311-318.
Scher et al., "Design and End Points of Clinical Trials for Patients With Progressive Prostate Cancer and Castrate Levels of Testosterone: Recommendations of the Prostate Cancer Clinical Trials Working Group", vol. 26, No. 7, Mar. 1, 2008, pp. 1148-1159.
Schweizer et al., "Abiraterone and other novel androgen-directed strategies for the treatment of prostate cancer: a new era of hormonal therapies is bom", Therapeutic Advances in Urology, vol. 4, No. 4, 2012, pp. 167-178.
Screenshot of webpage of Comprehensive Cancer Center Vienna regarding Abstract-Deadline of ESMA 2012 congress; accessible via: www.ccc.ac.at/news/singleview/kongress-deresmo-2012-in-wienabstract-deadline-ist-der-16-mai/ 04b878b896bfd0bbcfdab5498367 4ced/.
Small et al., "Prostate Specific Antigen Outcomes in Patients with Nonmetastatic Castration Resistant Prostate Cancer Treated with Apalutamide: Results from Phase 3 SPARTAN Study", presented at AUA 2018, May 18-21.
Table of Content, Annals of Oncology; Abstract Book of the 37th ESMO Congress, Kluver, Dordrecht, NL; Vienna, Austria, vol. 23, No. Suppl. 9, Sep. 17, 2012.
Vermorken et al., "Official Journal of the European Society for Medical Oncology and the Japanese Society of Medical Oncology", Annals of Oncology, vol. 23, No. 9, 2012, pp. i-ii.
Wayback Machine capture of https://www.esmo.org/events/vienna-2012-congress/abstract-submission.html, taken on Sep. 4, 2012.
"Prostate Cancer Clinical Practice Guidelines in Oncology NCCN Categories of Evidence and Consensus," Official Journal of the National Comprehensive Cancer Network, vol. 8, Issue 2, 2010.
Gura, "Cancer Models: Systems for Identifying New Drugs Are Often Faulty", Science, Nov. 1997, vol. 278, No. 5340, 1041-1042.
Higano, C. et al "Antitumor activity of MDV3100 in pre-and post-docetaxel advanced prostate cancer: long-term follow-up of the phase 1-2 study," (poster presented at American Society of Clinical Oncology Genitourinary Cancers Symposium, Orlando, FL, Chicago, IL, Feb. 17, 2011).
Hormonal Treatments for Uterine Fibroids (http://www.uterine-fibroids.org/Hormonal_Treatments.html, 2010).
Hwang et al., "Angiogenesis inhibitors in the treatment of prostate cancer", Journal of Hematology & Oncology, 2010, vol. 3, No. 26, 1-12.
Johnson et al., "Relationships between drug activity in NCI preclinical in vitro and in vivo models and early clinical trials", British Journal of Cancer, 2001, 84(10), 1424-1431.
Jung et al., Structure-activity relationship for thiohydantoin androgen receptor antagonists for castration-resistant prostate cancer (CRPC). J Med Chem. Apr. 8, 2010;53(7):2779-96. doi: 10.1021/jm901488g. Epub Sep. 27, 2011, 59 pages.
Kapoor, et al., BMC Cancer; A phase II randomized placebo-controlled double-blind study of salvage radiation therapy plus placebo versus SRT plus enzalutamide with high-risk PSA-recurrent prostate cancer after radical prostatectomy (SALV-ENZA); 2019; 10 pages.
Le et al. (2003). Plant-derived 3,3'-diindolylmethane Is a Strong Androgen Antagonist in Human Prostatic Cancer Cells. The Journal of Biological Chemistry, vol. 278(23), pp. 21136-21145.
LeRoith et al., "The insulin-like growth factor system and cancer", Cancer Letters, 2003, 195, 127-137.
Lodde, Michele, et al. Urologt 76 (5), 2010, pp. 1189-1193.
Lodish et al., "Endocrine side effects of broad-acting kinase inhibitors", Endocrine-Related Cancer, 2010, 17, R233-R244.
Madan et al. (2008). Analysis of Overall Survival in Patients with Nonmetastatic Castration-Resistant Prostate Cancer Treated with Vaccine, Nilutamide, and Combination Therapy. Cancer Therapy: Clinical, vol. 14(14), pp. 4526-4531.
Mammalian Cell Biotechnology: a Practical Approach, M. Butler, ed. (IRL Press, 1991).
Matthew R. Smith et al., "Apalutamide Treatment and Metastasis-free Survival in Prostate Cancer", The New England Journal of Medicine—NEJM—, Apr. 12, 2018, vol. 378, No. 15, pp. 1408-1418.
Mohler. J. L. et al., "Prostate Cancer, Version 3.2012," Journal of the National Comprehensive Cancer Network, vol. 10, Issue 9,2012, pp. 1081-1087.
Mukherji, D. et al. "Management of Metastatic Castration-Resistant Prostate Cancer," (2012) vol. 72, Issue 8, Cancer, pp. 1011-1028.
Naik et al., "Synthesis, Spectroscopic and Thermal Studies of Bivalent Transition Metal Complexes with the Hydrazone Derived from 2 Benzimidazolyl Mercaptoaceto Hydrazile and o-Hydroxy Aromatic Aldehyde", Indian Journal of Chemistry, 2008, 1793-1797.
News Release, 'Medivation and Astellas Announce Positive Survival Data from Interim Analysis of Phase 3 AFFIRM Trial of MDV3100 in Men with Advanced Prostate Cancer,' Nov. 3, 2011.
Okegawa et al., International Journal of Urology, 2010; 17:950-955 (Year: 2010).
Osanto et al., "Emerging novel therapies for advanced prostate cancer", Therapeutic Advances in Urology, 2012, vol. 4, No. 1,3-12.
Ouaissi et al., "Rationale for Possible Targeting of Histone Deacetylase Signaling in Cancer Diseases with a Special Reference to Pancreatic Cancer", Journal of Biomedicine and Biotechnology, 2011, 8 pages.
Presentation of Charles Sawyers, Prostate Cancer Foundation Scientific Retreat, Scottsdale, Arizona, Sep. 29-Oct. 1, 2005.
Rathkopf, D. et al. "946TiP—ARN-509 in Men with Metastatic Castration Resistant Prostate Cancer," (CRPC) vol. 23, (2012), (Supplement 9), Annals of Oncology, ix317.
Sarker et al., "Targeting the PI3K/AKT Pathway for the Treatment of Prostate Cancer", Clinical Cancer Research, 2009, vol. 15, No. 15, 4799-4805.
Sartor, Urology, 2003; 61 (Supppl 2A): 25-31.
Sartor; Progression of metastatic castrate-resistant prostate cancer: impact of therapeutic intervention in the post-docetaxel space Journal of Hematology & Oncology 2011, 4:18; 1-7.
Sauveur-Michel Maira et al., "Identification and characterization of NVP-BKM120, an orally available pan-class I PI3-kinase inhibitor", Molecular Cancer Therapeutics, vol. 11, No. 2, published on Dec. 21, 2011, pp. 317-328.

(56) References Cited

OTHER PUBLICATIONS

Sher, H.I. et al. "Increased Survival with Enzalutamide in Prostate Cancer after Chemotherapy," vol. 367, (2012), Issue 13, The New England Journal of Medicine, pp. 1187-1197.
Vargas, et al., The Journal of Nuclear Medicine; Reproducibility and Repeatability of Semiquantitative 18 F-Fluorodihydrotestosterone Uptake Metrics in Castration-Resistant Prostate Cancer Metastases: A Prospective Multicenter Study; Oct. 2018; vol. 59, No. 10; pp. 1516-1523.
Arneson, T.J., et al., "Androgen deprivation therapy (ADT) use in Medicare beneficiaries with nonmetastatic (M0) prostate cancer (PC) in the United States," Journal of Clinical Oncology, vol. 30, Issue 15, May 2012, pp. e15169-e15169 (Abstract).
Hager, J.H., et al., "Effect of the novel anti-androgen ARN-509 on response and seizure in castration-resistant prostate cancer models," Journal of Clinical Oncology, vol. 29, Issue 7, Mar. 2011 (abstract).
Labrie, F., et al., "Gonadotropin-Releasing Hormone Agonists in the Treatment of Prostate Cancer," Endocrine Reviews, vol. 26, No. 3, May 2005, pp. 361-379.
Massard, C., et al., "Targeting Continued Androgen Receptor Signaling in Prostate Cancer," Clinical Cancer Res., vol. 17, No. 12, Jun. 15, 2011, pp. 3876-3883.
Sundaram, S., et al., "Luteinizing hormone-releasing hormone receptor-targeted deslorelin-docetaxel conjugate enhances efficacy of docetaxel in prostate cancer therapy," Molecular Cancer Therapeutics, Vil. 8, No. 6, Jun. 2009, pp. 1655-1665.
"Influence of the revised FDA rules on the conclusion of a pharmaceutical related dispute", [03, 2006.01, 23, the date of search : Apr. 22, 2022], Retrieved at https://www.quinnjapan.com/news/articles/170323_01.html (documents indicating well-known arts) online],2017, 3 Pages.
Guidance for Industry,1999 , search date : Apr. 22, 2022, Retrieved at https://www.fda.gov/media/72419/download (documents indicating well-known arts) On Oct. 11, 15 Pages.
De Bono et al., "Abiraterone and Increased Survival in Metastatic Prostate Cancer", The New England Journal of Medicine, 2011, vol. 364, No. 21, pp. 1995-2005.
"Drugs@FDA: FDA-Approved Drugs," U.S. Food and Drug, retrieved at https://www.accessdata.fda.gov/scripts/cder/daf/index.cfm?event=overview.process&ApplNo=203415, retrieved on Aug. 31, 2012, p. 2.
"Hetero's letter regarding ANDA No. 217185" Apr. 18, 2022, p. 86.
"Zydus Pharmaceuticals letter regarding Erleada® (apalutamide) tablets, 60 mg ANDA No. 217113," Apr. 11, 2022, p. 83.
"Analysis of 695 Patent Application Claims." Annexure B, Apr. 1, 2021, p. 4.
"Analysis of 695 Patent Application Claims." Annexure C, Apr. 1, 2021, p. 4.
"Inconsistencies in the Mainwaring declaration," Jul. 6, 2021, p. 4.
Anonymous, "Highlights of prescribing information XTANDI", Jul. 1, 2018, pp. 1-29, XP055944718.
Clegg Nicola J et al: "Development of anti-androgen ARN-509 1 Supplemental Materials and Methods", Cancer Research, Mar. 1, 2012 (Mar. 1, 2012), pp. 1-13, XP055944437.
Response to Examination report for Australian Patent Application No. 2018206695 dated Jun. 3, 2020.
"ARN-509 Update: Phase I Study—Prostrate Cancer", HealingWell.com, 2014, 3 pages.
"Classification of Powders", The Pharmaceutics and Compounding Laboratory, http://pharmlabs.unc.edu/labs/powders/classification.htm, accessed Aug. 9, 2016, 2 pages.
"Fact Sheet—Prostrate-Specific Antigen (PSA) Test", 2014, National Cancer Institute, 6 pages.
"FDA ODAC Briefing Statement: Issues Concerning the Development of Products for the Treatment of Patients with Non-Metastatic Castration-Resistant Prostate Cancer", Sep. 14, 2011, 9 pages.
"Hormonal Treatments for Uterine Fibroids", Hormone Therapy for Fibroids, http://www.ulerine-fibroids.org/Hormonal_Treatments.html, 2010, 2 pages.
Alva et al., "I. Phase II study of Cilengitide (EMD 121974, NSC 707544) in Patients with Non-Metastatic Castration Resistant Prostate Cancer, NCI-6735. A study by the DOD/PCF Prostate Cancer Clinical Trials Consortium", Investigational New Drugs, 2012, 30(2), 749-757.
Amaral et al., "Castration-Resistant Prostate Cancer: Mechanisms, Targets, and Treatment", Hindawi Publishing Corporation, Prostate Cancer, Epub Mar. 5, 2012, vol. 2012, Article ID 327253, 11 pages.
Auricchio et al., "VAL 201—An Inhibitor of Androgen Receptor-associated Src and a Potential Treatment of Castration-resistant Prostate Cancer", European Oncology & Hematology, 2012, vol. 8, No. 1, 32-35.
Ausubel et al., "Current Protocols in Molecular Biology", Wiley Interscience Publishers, 1995, 2, 18 pages.
Baek et al., "Exchange of N-CoR Corepressor and Tip60 Coactivator Complexes Links Gene Expression by NF-kappaB and Beta-Amyloid Precursor Protein", Cell, 2002, 110, 55-67.
Balk, "Androgen Receptor as a Target in Androgen-Independent Prostate Cancer", Urology, 2002, 60(3A), 132-138.
Batch et al., "Androgen Receptor Gene Mutations Identified by SSCP in Fourteen Subjects with Androgen Insensitivity Syndrome", Hum. Mol. Genet., 1992, 1(7), 497-503.
Bohl et al., "Structural Basis for Antagonism and Resistance of Bicalutamide in Prostate Cancer", Proc. Nat. Acad. Sci., 2005, 102(17), 6201-6206.
Bredenberg et al., "New Concepts in Administration of Drugs in Tablet Form", Jan. 1, 2003, 83 pages.
Brockschmidt et al., "The Two Most Common Alleles of the Coding GGN Repeat in the Androgen Receptor Gene Cause Differences in Protein Function", J. Mol. Endocrinol., 2007, 39, 1-8.
Bundgaard, "Design of Application of Prodrugs", Harwood Academic Publishers, 1991, Chapter 5, 113-191.
Butler, "Mammalian Cell Biotechnology: A Practical Approach", 1991, 6 pages.
Cai et al., "c-Jun Has Multiple Enhancing Activities in the Novel Cross Talk Between the Androgen Receptor and ETS Variant Gene 1 in Prostate Cancer", Mol. Cancer Res., 2007, 5(7), 725-735.
Chang et al., "Molecular Cloning of Human and Rat Complementary DNA Encoding Androgen Receptors", Science, 1988, 240, 324-326.
Chobanian et al., "A Facile Microwave-Assisted Palladium-Catalyzed Cyanation of Aryl Chlorides", Tetrahed Lett., 2006, 47(19), 3303-3035.
Cinar et al. "Androgen Receptor Mediates the Reduced Tumor Growth, Enhanced Androgen Responsiveness, and Selected Target Gene Transactivation in Human Prostate Cancer Cell Line", Cancer Research, 2001, 61, 7310-7317.
Clegg et al., "ARN509: A Novel Antiandrogen for Prostate Cancer Treatment", Cancer Research, 2012, 72(6), 1494-1503.
Cook, "Development of GnRH Antagonists for Prostate Cancer: New Approaches to Treatment", The Oncologist Fundamentals of Cancer Medicine, 2000, vol. 5, 162-168.
Craft et al., "A Mechanism for Hormone-Independent Prostate Cancer Through Modulation of Androgen Receptor Signaling by the HER-2/Neu Tyrosine Kinase", Nature Medicine, 1999, 5(3), 280-285.
Craft et al., "Evidence for Clonal Outgrowth of Androgen-Independent Prostate Cancer Cells from Androgen-Dependent Tumors Through a Two-Step Process", Cancer Res, 1999, 59,5030-5036.
Creaven et al., "Pharmacokinetics and Metabolism of Nilutamide", Supp. Urology, 1991, 37(2), 13-19.
DePrimo et al. "Transcriptional Programs Activated by Exposure of Human Prostate Cancer Cells to Androgen", Genome Biology, 2002, 3(7), 1-12.
Dhal et al., "Synthesis of Thiohydantoins, Thiazolidones and their Derivatives from N1-(4'-aryl thiazole 2'-YL) Thioureas", J. Indian Chem. Soc., 1973, 50(1), 680-684.
Edwards et al., "Androgen Receptor Gene Amplification and Protein Expression in Hormone Refractory Prostate Cancer", British Journal of Cancer, 2003, 89, 552-556.
Ellis et al., "Characterization of a Novel Androgen-Sensitive, Prostate-Specific Antigen-Producing Prostatic Carcinoma Xenograft: LuCaP 23", Clin Cancer Res, 1996, 2, 1039-1048.

(56) References Cited

OTHER PUBLICATIONS

Ellwood-Yen et al., "Myc-Driven Murine Prostate Cancer Shares Molecular Features with Human Prostate Tumors", Cancer Cell, 2003, 4(3), 223-238.
Elokdah et al., "Design, Synthesis, and Biological Evaluation of Thio-Containing Compounds with Serum HDL-Cholesterol-Elevating Properties", J. Med. Chem., 2004, 47(3), 681-695.
Feher et al., "BHB: A Simple Knowledge-Based Scoring Function to Improve the C95 Efficiency of Database Screening", J. Chem. Inf. Comput. Sci., 2003, 43(4), 1316-1327.
Feldman et al., "The Development of Androgen-Independent Prostate Cancer", Nature Reviews Cancer, 2001, 1, 34-45.
Font de Mora et al., "AIB1 is a Conduit for Kinase-Mediated Growth Factor Signaling to the Estrogen Receptor", Mol. Cell. Biol., 2000, 20(14), 5041-5047.
Foury et al., "Control of the Proliferation of Prostate Cancer Cells by an Androgen and Two Antiandrogens. Cell Specific Sets of Responses", J. Steroid Biochem. Molec. Bioi., 1998, 66(4), 235-240.
Gelmann, "Molecular Biology of the Androgen Receptor", J. Clin. Oncol., 2002, 20, 3001-3015.
Gioeli et al., "Androgen Receptor Phosphorylation Regulation and Identification of the Phosphorylation Sites", J Biol Chem, 2002, 277(32), 29304-29314.
Glass et al., "The Coregulator Exchange on Transcriptional Functions of Nuclear Receptors", Genes Dev., 2000, 14, 121-141.
Godbole et al., "New Insights into the Androgen-Targeted Therapies and Epigenetic Therapies in Prostate Cancer", Prostate Cancer, 2011, 1-13.
Goubet et al., "Conversion of a Thiohydantoin to the Corresponding Hydantoin via a Ring-Opening/Ring Closure Mechanism", Tetrahedron Letters, 1996, 37(43), 7727-7730.
Grad et al., "Multiple Androgen Response Elements and a Myc Consensus Site in the Androgen Receptor (AR) Coding Region are Involved in Androgen-Mediated Up-Regulation of AR Messenger RNA", Mol Endocrinol, 1999, 13, 1896-1911.
Graham et al., "A New Technique for the Assay of Infectivity of Human Adenovirus 5 DNA", Virology, 1973, 52, 456-467.
Gregory et al., "A Mechanism for Androgen Receptor-Mediated Prostate Cancer Recurrence After Androgen Deprivation Therapy", Cancer Res., 2001, 61, 4315-4319.
Gregory et al., "Androgen Receptor Stabilization in Recurrent Prostate Cancer is Associated with Hypersensitivity to Low Androgen", Cancer Res, 2001, 61, 2892-2898.
Hamilton-Reeves et al, "Isoflavone-Rich Soy Protein Isolate Suppresses Androgen Receptor Expression Without Altering Estrogen Receptor-Beta Expression or Serum Hormonal Profiles in Men at High Risk of Prostate Cancer", J. Nutr., 2007, 137, 1769-1775.
Higuchi et al., "Pro-Drugs as Novel Delivery Systems", 1975, vol. 14 of the A.C.S. Symposium Series, 6 pages.
Holzbeierlein et al., "Gene Expression Analysis of Human Prostate Carcinoma During Hormonal Therapy Identifies Androgen-Responsive Genes and Mechanisms of Therapy Resistance", Am. J. Pathology, 2004, 164(1), 217-227.
Homma et al., "Differential Levels of Human Leukocyte Antigen-Class I, Multidrugresistance 1 and Androgen Receptor Expressions in Untreated Prostate Cancer Cells: The Robustness of Prostate Cancer", Oncol. Rep., 2007, 18, 343-346.
Hong et al., "Non Metastatic Castration-Resistant Prostrate Cancer", Korean Journal of Urology, 2014, 55, 153-160.
Horoszewicz et al., "LNCaP Model of Human Prostatic Carcinoma", Cancer Res., 1983, 43, 1809-1818.
Huang et al., "AR Possess an Intrinsic Hormone-Independent Transcriptional Activity", Mol Endocrinol., 2002, 16(5), 924-937.
Jones, "Proteinase Mutants of *Saccharomyces cerevisae*", Genetics, 1977, 85, 23-33.
Kagabu, "Methyl, Trifluoromethyl, and Methoxycarbonyl-Introduction to the Fifth Position on the Pyridine Ring of Chloronicotinyl Insecticide Imidacloprid", Synth Comm. 2006, 36(9), 1235-1245.
Karvonen et al., "Interaction of Androgen Receptors with Androgen Response Element in Intact Cells", The Journal of Biological Chemistry, 1997, 272(25), 15973-15979.
Kato et al., "Activation of the Estrogen Receptor through Phosphorylation by Mitogenactivated Protein Kinase", Science, 1995, 270, 1491-1494.
Kawai et al., "Site-Specific Fluorescent Labeling of Rna Molecules by Specific Transcription Using Unnatural Base Pairs", J. Am Chem. Soc., 2005, 127(49), 17286-17295.
Kemppainen et al., "Distinguishing Androgen Receptor Agonists and Antagonists: Distinct Mechanisms of Activation by Medroxyprogesterone Acetate and Dihydrotestosterone", Mol. Endocrinol., 1999, 13, 440-454.
Keown et al., "Methods for Introducing DNA Into Mammalian Cells", Methods in Enzymology, 1990, 185, 527-537.
Kingsman et al., "Replication in *Saccharomyces cerevisiae* of Plasmid pBR313 Carrying DNA from the Yeast trpl REGION", Gene, 1979, 7, 141-152.
Kinoshita et al., "Methylation of the Androgen Receptor Minimal Promoter Silences Transcription in Human Prostate Cancer", Cancer Res, 2000, 60, 3623-3630.
Klein et al., "Progression of Metastatic Human Prostate Cancer to Androgen Independence in Immunodeficient SCID Mice", Nat Med, 1997, 3(4), 402-408.
Kliment, "Re: Salvage Therapy with Bicalutamide 150 mg in Nonmetastatic Castration-Resistant Prostate Cancer", European Urology, 2011, 59(6), 1066-1067.
Kousteni et al., "Nongenotropic, Sex-Nonspecific Signaling through the Estrogen or Androgen Receptors: Dissociation from Transcriptional Activity", Cell, 2001, 104, 719-730.
Kuethe et al., "Synthesis of Disubstituted Imidazo[4,5-b]pyridin-2-ones", J. Org. Chem., 2004, 29, 69(22), 7752-7754.
Laitinen et al., "Chromosomal Aberrations in Prostate Cancer Xenografts Detected by Comparative Genomic Hybridization", Genes Chromosomes Cancer, 2002, 35, 66-73.
Li et al., "Heterogeneous Expression and Functions of Androgen Receptor Co-Factors in Primary Prostate Cancer", Am J Pathol, 2002, 161(4), 1467-1474.
Linja et al., "Amplification and Overexpression of Androgen Receptor Gene in Hormone-Refractory Prostate Cancer", Cancer Research, 2001, 61, 3550-3555.
Liu et al., "Lineage relationship between LNCaP and LNCaPderived prostate cancer cell lines", Prostate, Jul. 1, 2004, 60(2), 98-108.
Lobaccaro et al., "Molecular Modeling and In Vitro Investigations of the Human Androgen Receptor DNA-Binding Domain: Application for the Study of Two Mutations", Mol. Cell. Endocrinol., 1996, 116, 137-147.
Mansour et al., "Disruption of the Proto-Oncogene int-2 in Mouse Embryo-Derived Stem Cells: A General Strategy for Targeting Mutations to Non-Selectable Genes", Nature, 1988, 336, 348-352.
Marhefka et al., "Homology Modeling Using Multiple Molecular Dynamics Simulations and Docking Studies of the Human Androgen Receptor Ligand Binding Domain Bound to Testosterone and Nonsteroidal Ligands", J. Med. Chem., 2001, 44(11), 1729-1740.
Masiello et al., "Bicalutamide Functions as an Androgen Receptor Antagonist by Assembly of a Transcriptionally Inactive Receptor", J Biol Chem, 2002, 277(29), 26321-26326.
Matias et al., "Local Inhibition of Sebaceous Gland Growth by Topically Applied RU 58841", NY Acad. Sci., 1995, 761, 56-65.
Matias et al., "Structural Basis for the Glucocorticoid Response in a Mutant Human Androgen Receptor (AR(ccr)) Derived from an Androgen-Independent Prostate Cancer", J Med Chem, 2002, 45, 1439-1446.
Matias et al., "Structural Evidence for Ligand Specificity in the Binding Domain of the Human Androgen Receptor: Implications for Pathogenic Gene Mutations", J Biol Chem, 2000, 275(34), 26164-26171.
McDonnell et al., "Expression of the Protooncogene bcl-2 in the Prostate and its Association with Emergence of Androgen-Independent Prostate Cancer", Cancer Res, 1992, 52, 6940-6944.
Migliaccio et al., "Steroid-Induced Androgen Receptor-Oestradiol Receptor beta-SRC Complex Triggers Prostate Cancer Cell Proliferation", Embo J, 2000, 19(20), 5406-5417.

(56) References Cited

OTHER PUBLICATIONS

Millennium-Takeda, "Press Release: Clinical Data Presented on Orteronel (TAK-700) Without Steroids in Non-Metastatic Prostrate Cancer", 2012, 2 pages.
Morgan et al., "(RAD001 (Everolimus) Inhibits Growth of Prostate Cancer in the Bone and the Inhibitory Effects Are Increased by Combination With Doxetaxel and Zoledronic Acid", The Prostate, Jun. 1, 2008, 861-871.
Mulholland et al., "Cell Autonomous Role of PTEN in Regulating Castration-Resistant Prostate Cancer Growth", Cancer Cell., 2011, 19, 792-804.
Muller et al., "BCR First Exon Sequences Specifically Activate the BCRIABL Tyrosine Kinase Oncogene of Philadelphia ChromosomePositive Human Leukemias", Mol. & Cell, Biol., 1991, 11(4), 1785-1792.
Nam et al., "Action of the Src Family Kinase Inhibitor, Dasatinib (BMS-354825), on Human Prostate Cancer Cells", Cancer Res., 2005, 65(20), 9185-9189.
Navone et al., "Model Systems of Prostate Cancer: Uses and Limitations", Cancer Metastasis, 1999, 17, 361-371.
NCBI, "Definition: *Homo sapiens* Androgen", Nucleotide, 2007, 7 pages NM_000044<http://www.ncbi.nlm.nih.gov:80/entrez/viewer.fcgi?cmd=Retrieve&db=nucleotide&list_ u ids=21322251&dopt=Gen Bank&term=sapiens+AR+androgen+receptor+prostate+cancer&qty=1>gi:21322251.
Norris et al. "Peptide Antagonists of the Human Estrogen Receptor", Science, 1999, 285, 744-746.
Ouk et al., "Development of Androgen Receptor Inhibitors for Hormone-Refractory Prostate Cancer", Prostate Cancer Foundation Meeting, Scottsdale, AZ, Sep. 29-Oct. 1, 2005, 1 page.
Perou et al., "Molecular Portraits of Human Breast Tumors", Nature, 2000, 406, 747-752.
Prostate-Specific Antigen (PSA) Test, National Cancer Institute, 2012, 6 pages.
Raffo et al., "Overexpression of bcl-2 Protects Prostate Cancer Cells from Apoptosis in Vitro and Confers Resistance to Androgen Depletion in Vivo", Cancer Research, 1995, 55, 4438-4445.
Rathkopf et al., "A First-In-Human. Open-Label. Phase 1/11 Safety. Pharmacokinetic and Proof-of-Concept Study of ARN-509 in Patients with Progressive Advanced Castration-Resistant Prostate Cancer (CRPC )", J. of Clin. Oncol.; ASCO Annual Meeting, 2011, 29(15), 2 pages.
Rathkopf et al., "A Phase I Study of the Androgen Signaling Inhibitor ARN-509 in Patients with Metastatic Castration-Resistant Prostate Cancer (mCRPC)", J. Clin. Oncol., 2012, 2 pages.
Rathkopf et al.: "Phase I/II safety and pharmacokinetic (PK) study of ARN-509 in patients with metastatic castration-resistant prostate cancer (mCRPC): Phase I results of a Prostate Cancer Clinical Trials Consortium study", Journal of Clinical Oncology, Feb. 2012, vol. 30, No. 5 Supplement, Abstract 43, 2 pages.
Rathkopf et al: "A phase II study of the androgen signaling inhibitor ARN-509 in patients with castration-resistant prostate cancer (CRPC)", Journal of Clinical Oncology, May 2012 Annual Meeting of the American Society of Clinical Oncology, ASCO, vol. 30, No. 15 Supplement, Abstract TPS4697, 1 page.
ReaganShaw et al, "Dose Translation from Animal to Human Studies Revisited", 2007, 22, 659-661.
Remington: Practice of the Science and Pharmacy, 19th Edition, Table of Contents, Gennaro (ed.), 1995, Mack Publishing Company, Easton, PA, 5 pages.
Rooseboom et al., "Enzyme-Catalyzed Activation of Anticancer Prodrugs", Pharmacological Reviews, 2004, 56, 53-102.
Ryan et al., "Abiraterone in Metastatic Prostate Cancer without Previous Chemotherapy", New England Journal of Medicine, Jan. 10, 2013, vol. 368, No. 2, 138-148.
Sack et al., "Crystallographic Structures of the Ligand-Binding Domains of the Androgen Receptor and its T877A Mutant Complexed with the Natural Agonist Dihydrotestosterone", Proc Natl Acad Sci, 2001, 98(9), 4904-4909.
Sambrook et al., "Molecular Cloning: A Laboratory Manual", 2nd Edition, Table of Contents, Cold Spring Harbor Laboratory Press, Cold Spring Harbor, 1989, 30 pages.
Saunders et al., "Point Mutations Detected in the Androgen Receptor Gene of Three Men with Partial Androgen Insensitivity Syndrome", Clin. Endocrinol., 1992, 37, 214-220.
Schellhammer et al., "Prostate Specific Antigen Decreases after Withdrawal of Antiandrogen Therapy with Bicalutamide or Flutamide in Patients Receiving Combined Androgen Blockade", J Urol, 1997, 157, 1731-1735.
Scher et al., "Antitumour activity of MDV3100 in castration-resistant prostate cancer: a phase 1-2 study", Lancet, Apr. 24, 2010, 375(9724), 1437-1446.
Scher et al., "The Flutamide Withdrawal Syndrome: Its Impact on Clinical Trials in Hormone-Refractory Prostatic Cancer", J Clin Oncol 1993, 11, 1566-1572.
Sderholm et al., "Three-Dimensional Structure-Activity Relationships of Nonsteroidal Ligands in Complex with Androgen Receptor Ligand-Binding Domain," J. Med. Chem., 2005, 48(4), 917-925.
Shang et al., "Formation of the Androgen Receptor Transcription Complex", Mol Cell, 2002, 9, 601-610.
Shang et al., "Molecular Determinants for the Tissue Specificity of SERMs", Science, 2002, 295, 2465-2468.
Shi et al., "Functional Analysis of 44 Mutant Androgen Receptors from Human Prostate Cancer", Can Res, 2002, 62(5), 1496-1502.
Shiau et al., "The Structural Basis of Estrogen Receptor/Coactivator Recognition and the Antagonism of this Interaction by Tamoxifen", Cell, 1998, 95, 927-937.
Singh et al., "Androgen Receptor Antagonists (Antiandrogens): Structure-Activity Relationships", Current Medicinal Chemistry, 2000, 7, 211-247.
Smith et al., "ARN-509 in Men with High Risk Non-Metastatic Castration-Resistant Prostate Cancer", Annals of Oncology; Abstract Book of the 37th ESMO Congress, 2012, 23(9), No. Suppl. 9, 1 page.
Smith et al., "ARN-509 in Men with High Risk Non-Metastatic Castration-Resistant Prostate Cancer", European Journal of Cancer; European Cancer Congress, 2013, 49(2), 1 page.
Smith, "ARN-509 in Men with High Risk Non-Metastatic Castration-Resistant Prostate Cancer", Massachusetts General Hospital, Harvard Medical School, 2012, 1 page.
Soto et al., "Control of Cell Proliferation: Evidence for Negative Control on C141 Estrogen-Sensitive T47D Human Breast Cancer Cells", Cancer Research, 1986, 46, 2271-2275.
Sperry et al., Androgen Binding Profiles of Two Distinct Nuclear Androgen Receptors in Atlantic Croaker (*Micropogonias undulates*), Journal of Steroid Biochemistry & Molecular Biology, 2000, 73, 93-103.
Stinchcomb et al., "Isolation and Characterisation of a Yeast Chromosomal Replicator", 1979, 282, 39-43.
Su et al., "Polymorphisms of Androgen Receptor Gene in Childhood and Adolescent Males with First-Onset Major Depressive Disorder and Association with Related Symptomatology", Int. J. Neurosci., 2007, 117, 903-917.
Sweet et al., "A Unique Point Mutation in the Androgen Receptor Gene in a Family with Complete Androgen Insensitivity Syndrome", Fertil. Steril., 1992, 58(4), 703-707.
Szelei et al., "Androgen-Induced Inhibition of Proliferation in Human Breast Cancer MCF7 C138b Cells Transfected with Androgen Receptor", Endocrinology, 1997, 138(4), 1406-1412.
Takemoto et al., "Novel Pottasium Chanel Openers: Synthesis and Pharmacological Evaluation of New N-(substituted-3-pyridyl)-N'-alkylthioureas and Related Compounds", J Med. Chem., 1994, 37(1), 18-25.
Taplin et al. "Selection for Androgen Receptor Mutations in Prostate Cancers Treated with Androgen Antagonist", Cancer Res, 1999, 59, 2511-2555.
Taplin et al., "Androgen Receptor Mutations in Androgen-Independent Prostate Cancer: Cancer and Leukemia Group B Study 9663", J Clin Oncol, 2003, 21, 2673-2678.
Taplin et al., "Mutation of the Androgen-Receptor Gene in Metastatic Androgen Independent Prostate Cancer", N Engl J Med, 1995, 332(21), 1393-1398.

(56) References Cited

OTHER PUBLICATIONS

Teutsch et al., "Non-steroidal Antiandrogens: Synthesis and Biological Profile of High-affinity Ligands for the Androgen Receptor", J. Steroid Biochem. Mol. Biol., 1994, 48,111-119.
Tran et al., "Development of a Second-Generation Antiandrogen for Treatment of Advanced Prostate Cancer", Science, 2009, 324(5928), 787-790.
Tremblay et al., "Ligand-Independent Recruitment of SRC-1 to Estrogen Receptor Beta through Phosphorylation of Activation Function AF-1", Mol Cell, 1999, 3, 513-519.
Tschumper et al., "Sequence of a Yeast DNA Fragment Containing a Chromosomal Replicator and the TRP1 Gene", Gene, 1980, 10, 157-166.
Urlaub et al., "Isolation of Chinese Hamster Cell Mutants Deficient in Dihydrofolate Reductase Activity", Proc. Natl. Acad. Sci. USA, 1980, 77(7), 4216-4220.
Van Dort et al., "Design, Synthesis, and Pharmacological Characterization of 4-[ 4,4-Dimethyl-3-( 4-hydroxybutyl)-5-oxo-2-thioxo-1-imidazolidinyl]-2-iodobenzonitrile as a High-Affinity Nonsteroidal Androgen Receptor Ligand", J. Med. Chem., 2000, 43, 3344-3347.
Veldscholte et al., "A Mutation in the Ligand Binding Domain of the Androgen Receptor of Human LNCaP Cells Affects Steroid Binding Characteristics and Response to Antiandrogens", Biochem Biophys Res Commun, 1990, 173, 534-540.
Visakorpi et al., "In Vivo Amplification of the Androgen Receptor Gene and Progression of Human Prostate Cancer", Nat Genetics, 1995, 9, 401-406.
Wainstein et al., "CWR22: Androgen-Dependent Xenograft Model Derived from a Primary Human Prostatic Carcinoma", Cancer Res, 1994, 54, 6049-6052.
Wallen et al., "Androgen Receptor Gene Mutations in Hormone-Refractory Prostate Cancer", J. Pathology, 1999, 189, 559-563.
Wang et al., "Overexpressed Androgen Receptor Linked to p21WAF1 Silencing May Be Responsible for Androgen Independence and Resistance to Apoptosis of a Prostate Cancer Cell Line", Cancer Research, 2001, 61(20), 7544-7551.
Wang et al., "Prostate-Specific Deletion of the Murine Pten Tumor Suppressor Gene Leads to Metastatic Prostate Cancer", Cancer Cell, 2003, 4, 209-221.
Wermuth et al., "Designing Prodrugs and Bioprecursors, I: Carrier Prodrugs", The Pharmacological Basis of Therapeutics, The Practice of Medicinal Chemistry, Goodman and Gilman, eds., Macmillan Publishing Co., New York, Chapter 31, 1996, 28 pages.
Wermuth, "Molecular Variations Based on Isosteric Replacements", The Practice of Medicinal Chemistry, 1996, 13, 203-237.
Wooster et al., "A Germline Mutation in the Androgen Receptor Gene in Two Brothers with Breast Cancer and Reifenstein Syndrome", Nat. Genet., 1992, 2, 132-134.
Zakikhani et al., "Metformin is an AMP Kinase-Dependent Growth Inhibitor for Breast Cancer Cells", Cancer Res, 2006, 66(21), 10269-10273.
Zarghami et al., "Steroid Hormone Regulation of Prostate-Specific Antigen Gene Expression in Breast Cancer", British Journal of Cancer, 1997, 75(4), 579-588.
Zhau et al., "Androgen-Repressed Phenotype in Human Prostate Cancer", Proc Natl Acad Sci USA, 1996, 93,15152-15157.
Zhou et al., "A Ligand-Dependent Bipartite Nuclear Targeting Signal in the Human Androgen Receptor, Requirement for the DNA-Binding Domain and Modulation by NH2-Terminal and Carboxyl-Terminal Sequences", J Bio Chem, 1994, 269(18), 13115-13123.
Zoppi et al., "Amino Acid Substitutions in the DNA-Binding Domain of the Human Androgen Receptor are a Frequent Cause of Receptor-Binding Positive Androgen Resistance", Mol. Endo., 1992, 6, 409-415.

* cited by examiner

ANTI-ANDROGENS FOR THE TREATMENT OF NON-METASTATIC CASTRATE-RESISTANT PROSTATE CANCER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is a continuation of U.S. patent application Ser. No. 14/034,460 filed Sep. 23, 2013, which claims priority to U.S. Patent Application Ser. No. 61/705,900, filed Sep. 26, 2012, the contents of which are incorporated by reference herein in its entirety for all purposes

FIELD OF THE INVENTION

Described herein are methods of treating non-metastatic castrate-resistant prostate cancer with anti-androgens, including but not limited to, 4-[7-(6-cyano-5-trifluoromethylpyridin-3-yl)-8-oxo-6-thioxo -5,7 -diazaspiro[3.4]oct-5-yl]-2-fluoro-N-methylbenzamide.

BACKGROUND OF THE INVENTION

Prostate cancer is the second most frequently diagnosed cancer and the second leading cause of cancer death in males. The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state.

SUMMARY OF THE INVENTION

In one aspect, described herein is a method of treating non-metastatic castration-resistant prostate cancer in a male human comprising administering a therapeutically effective amount of an anti-androgen to a male human with non-metastatic castration-resistant prostate cancer. In some embodiments, wherein the non-metastatic castration-resistant prostate cancer is high risk non-metastatic castration-resistant prostate cancer. In some embodiments, the male human with high risk non-metastatic castration-resistant prostate cancer has a prostate-specific antigen doubling time (PSADT) that is less than or equal to 10 months. In some embodiments, administration of the anti-androgen provides an increase in the metastasis-free survival of the male human.

In another aspect, described herein is a method of providing an increase in the metastasis-free survival of a male human with prostate cancer comprising administering a therapeutically effective amount of an anti-androgen to the male human with prostate cancer. In some embodiments, the prostate cancer is non-metastatic castration-resistant prostate cancer. In some embodiments, the prostate cancer is high risk non-metastatic castration-resistant prostate cancer. In some embodiments, the male human with high risk non-metastatic castration-resistant prostate cancer has a prostate-specific antigen doubling time (PSADT) that is less than or equal to 10 months.

In some embodiments, the anti-androgen is a non-steroidal anti-androgen.

In some embodiments, the anti-androgen binds directly to the ligand-binding domain of the androgen receptor.

In some embodiments, the anti-androgen is a second-generation anti-androgen.

In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide; 4-(3-(4-cyano-3-(trifluoromethyl)phenyl)-5,5-dimethyl-4-oxo-2-thioxoimidazolidin-1-yl)-2-fluoro-N-methylbenzamide (enzalutamide); or 4-[7-(4-cyano-3-trifluoromethylphenyl)-8-oxo-6-thioxo-5,7-diazaspiro[3.4]oct-5-yl]-2-fluoro-N-methylbenzamide (RD162).

In some embodiments, the anti-androgen is administered orally to the male human. In some embodiments, the anti-androgen is administered to the male human in the form of a tablet, a pill, a capsule, a solution, a suspension, or a dispersion. In some embodiments, the anti-androgen is administered to the male human on a continuous daily dosing schedule.

In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, or about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

In any of the embodiments described herein, the methods of treatment further comprises administering a gonadotropin-releasing hormone (GnRH) agonist. In some embodiments, the GnRH agonist is leuprolide, buserelin, nafarelin, histrelin, goserelin, or deslorelin.

In any of the aforementioned aspects the effective amount of the anti-androgen is: (a) systemically administered to the male human; and/or (b) administered orally to the male human; and/or (c) intravenously administered to the male human; and/or (d) administered by injection to the male human.

In any of the aforementioned aspects, the effective amount of the anti-androgen is administered (i) once a day; or (ii) multiple times over the span of one day. In some embodiments, the effective amount of the anti-androgen is administered once a day, twice a day, three times a day or four times a day.

In any of the aforementioned aspects the effective amount of the anti-androgen is administered continuously or intermittently. In some embodiments, the effective amount of the anti-androgen is administered continuously. In some embodiments, the effective amount of the anti-androgen is administered daily.

In some embodiments, compounds provided herein are orally administered.

Other objects, features and advantages of the methods, uses and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5α-dihydrotestosterone (5α-DHT).

The androgen receptor (AR), located on Xq11-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However androgen depletion is usually effective for a limited duration and prostate cancer evolves to regain the ability to grow despite low levels of circulating androgens. Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g. GnRH agonists), alone or in combination with anti-androgens (e.g. bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC)

to which most patients eventually succumb. Recent studies on the molecular basis of CRPC have demonstrated that CRPC continues to depend on AR signaling and that a key mechanism of acquired resistance is an elevated level of AR protein (Nat. Med, 2004, 10, 33-39). AR targeting agents with activity in castration sensitive and castration resistant resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (Science, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (J Clin Oncol, 1993. 11(8): p. 1566-72).

Prostate Cancer Stages

In the early stages of prostate cancer, the cancer is localized to the prostate. In these early stages, treatment typically involves either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer are treated with agents that block the production of testosterone (eg, GnRH agonists), alone or in combination with anti-androgens (eg, bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb.

Castration-resistant prostate cancer (CRPC) is categorized as non-metastatic or metastatic, depending on whether or not the prostate cancer has metastasized to other parts of the body.

In some embodiments, prior to treatment with a second-generation anti-androgen men with non-metastatic CRPC are characterized as having the following:

1. Histologically or cytologically confirmed adenocarcinoma of the prostate without neuroendocrine differentiation or small cell features, with high risk for development of metastases.
2. Castration-resistant prostate cancer demonstrated during continuous androgen deprivation therapy (ADT)/post orchiectomy. For example defined as 3 consecutive rises of PSA, 1 week apart, resulting in two 50% increases over the nadir, with the last PSA >2 ng/mL.
3. Maintain castrate levels of testosterone (<50 ng/dL [1.72 nmol/L]) within 4 weeks of randomization and throughout the study.
4. Absence of distant metastasis by bone scan, CT or MRI scans.

Anti-Androgens

As used herein, the term "anti-androgen" refers to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity of a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity of a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro[3.4]oct-5-yl]-2-fluoro-N-methylbenzamide (also known as ARN-509; CAS No. 956104-40-8); 4-(3-(4-cyano-3-(trifluoromethyl)phenyl)-5,5-dimethyl-4-oxo-2-thioxoimidazolidin-1-yl)-2-fluoro-N-methylbenzamide (also known as MDV3100 or enzalutamide; CAS No: 915087-33-1) and 4-[7-(4-cyano-3-trifluoromethylphenyl)-8-oxo-6-thioxo-5,7-diazaspiro[3.4]oct-5-yl]-2-fluoro-N-methylbenzamide (RD162; CAS No. 915087-27-3). In some embodiments, a second-generation anti-androgen binds to an AR polypeptide at or near the ligand binding site of the AR polypeptide.

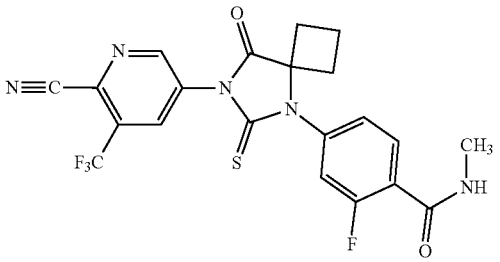

4-[7-(6-cyano-5-trifluoromethylpyridin-3-yl)-8-oxo-6-thioxo-5,7-diazaspiro[3,4]oct-5-yl]-2-fluoro-N-methylbenzamide (ARN-509)

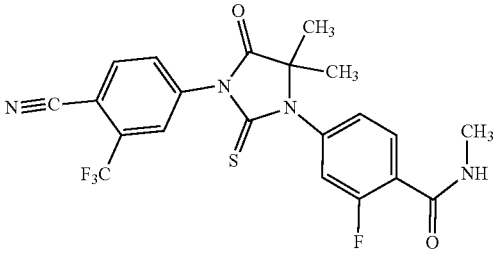

4-(3-(4-cyano-3-(trifluoromethyl)phenyl)-5,5-dimethyl-4-oxo-2-thioxoimidazolidin-1-yl)-2-fluoro-N-methylbenzamide (enzalutamide)

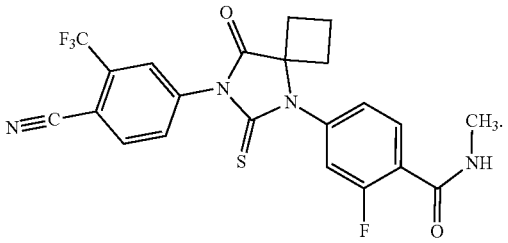

4-[7-(4-cyano-3-trifluoromethylphenyl)-8-oxo-6-thioxo-5,7-diazaspiro[3,4]oct-5-yl]-2-fluoro-N-methylbenzamide (RD162)

In some embodiments, an anti-androgen contemplated in the methods described herein inhibits AR nuclear translocation, DNA binding to androgen response elements, and coactivator recruitment. In some embodiments, an anti-androgen contemplated in the methods described herein exhibits no agonist activity in AR-overexpressing prostate cancer cells.

4-[7-(6-Cyano-5-trifluoromethylpyridin-3-yl)-8-oxo-6-thioxo-5,7-diazaspiro[3.4]oct-5-yl]-2-fluoro-N-methylbenzamide 4-[7-(6-Cyano-5-trifluoromethylpyridin-3-yl)-8-oxo-6-thioxo-5,7-diazaspiro[3.4]oct-5-yl]-2-fluoro-N-methylbenzamide is a second-generation anti-androgen that binds directly to the ligand-binding domain of AR, impairing nuclear translocation, AR binding to DNA and AR target gene modulation, thereby inhibiting tumor growth and promoting apoptosis. 4-[7-(6-Cyano-5-trifluoromethylpyridin-3-yl)-8-oxo-6-thioxo-5,7-diazaspiro[3.4]oct-5-yl]-2-fluoro-N-methylbenzamide binds AR with greater affinity than bicalutamide, and induces partial or complete tumor regression in non-castrate hormone-sensitive and bicalutamide-resistant human prostate cancer xenograft models (Clegg et al. Cancer Res Mar. 15, 2012 72; 1494). 4-[7-(6-Cyano-5-trifluoromethylpyridin-3-yl)-8-oxo-6-thioxo-5,7-diazaspiro[3.4]oct-5-yl]-2-fluoro-N-methylbenzamide lacks the partial agonist activity seen with bicalutamide in the context of AR overexpression.

Disclosed herein is the use of 4-[7-(6-Cyano-5-trifluoromethylpyridin-3-yl)-8-oxo-6-thioxo-5,7-diazaspiro[3.4]oct-5-yl]-2-fluoro-N-methylbenzamide in the treatment of non-metastatic castration-resistant prostate cancer in a male human.

Also described herein, is the use of a second-generation anti-androgen in the treatment of non-metastatic castration-resistant prostate cancer in a male human.

In a Phase II clinical trial of male humans with non-metastatic castration-resistant prostate cancer, oral administration of 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule resulted in a ≥50% decline in PSA from baseline at week 12 (i.e. about 3 months) in a portion of the patients. At 3 months, a PSA50 (i.e. ≥50% decline in PSA from baseline)

and a PSA90 (i.e. ≥90% decline in PSA from baseline) were observed in 91% and 38% of the males that were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule, respectively. At 6 months, a PSA50 and a PSA90 were observed in 91% and 55% of the males that were orally administered 240 mg of 4-[7-(6-cyano-5-trifluoromethylpyridin-3-yl)-8-oxo-6-thioxo-5,7-diazaspiro[3.4]oct-5-yl]-2-fluoro-N-methylbenzamide on a continuous daily dosing schedule, respectively.

Certain Terminology

Throughout this specification, words are to be afforded their normal meaning, as would be understood by those skilled in the relevant art. However, so as to avoid misunderstanding, the meanings of certain terms will be specifically defined or clarified.

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "NM-CRPC" as used herein refers to non-metastatic castration-resistant prostate cancer. In some embodiments, NM-CRPC is assessed with bone scan and computed tomography (CT) or magnetic resonance imaging (MRI) scans.

The term "high risk NM-CRPC" as used herein refers to probability of a man with NM-CRPC developing metastases. In some embodiments, high risk for development of metastases is defined as prostate specific antigen doubling time (PSADT) ≤20 months, ≤19 months, ≤18 months, ≤17 months, ≤16 months, ≤15 months, ≤14 months, ≤13 months, ≤12 months, or ≤11 months, ≤10 months, ≤9 months, ≤8 months, ≤7 months, ≤6 months, ≤5 months, ≤4 months, ≤3 months, ≤2 months, or ≤1 month. In some embodiments, high risk for development of metastases is defined as prostate specific antigen doubling time (PSADT) ≤10 months.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an anti-androgen being administered which will relieve to some extent one or more of the symptoms of the disease or condition being treated. The result can be reduction and/or alleviation of the signs, symptoms, or causes of a disease, or any other desired alteration of a biological system. For example, an effective amount of an anti-androgen is the amount of the anti-androgen that after administration for 3 months to a male human with non-metastatic castration-resistant prostate cancer provides a PSA50 or PSA90 or demonstrates a robust (such as ≥90%) AR blockade (e.g. by FDHT-PET). In some embodiments, an effective amount of an anti-androgen is the amount of the anti-androgen that after administration for 6 months to a male human with non-metastatic castration-resistant prostate cancer provides a PSA50 or PSA90. In some embodiments, the anti-androgen is administered on a continuous daily dosing schedule. An appropriate "effective" amount in any individual case may be determined using techniques, such as a dose escalation study.

The term "FDHT-PET" refers to 18F-16β-fluoro-5α-dihydrotestosterone Positron Emission Tomography and is a technique that uses a tracer based on dihydrotestosterone, and allows for a visual assessment of ligand binding to the androgen receptor in a patient. It may be used to evaluate pharmacodynamics of an androgen receptor directed therapy The term "continuous daily dosing schedule" refers to the administration of an anti-androgen daily without any drug holidays. In some embodiments, a continuous daily dosing schedule comprises administration of an anti-androgen everyday at roughly the same time each day.

The terms "treat," "treating" or "treatment," as used herein, include alleviating, abating or ameliorating at least one symptom of a disease disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, in the context of administering an anti-androgen to a male human with NM-CRPC, treating comprises any one, or a combination, of the following: providing a PSA50 or PSA90 in men with NM-CRPC as compared to placebo at 3 months; providing a PSA50 or PSA90 in men with NM-CRPC as compared to placebo at 6 months; demonstrating superiority in the metastasis-free survival (MFS) of men with NM-CRPC as compared to placebo (i.e. not administering a second-generation anti-androgen); increasing the overall survival (OS) of men with NM-CRPC as compared to placebo; increasing the time to metastasis (TTM) in men with NM-CRPC as compared to placebo; increasing the progression-free survival (PFS) in men with NM-CRPC as compared to placebo; increasing the time to PSA progression (TTPP) in men with NM-CRPC as compared to placebo; increasing the health-related quality of life and prostate cancer-specific symptoms in men with NM-CRPC as compared to placebo. In some embodiments, the NM-CRPC is high-risk NM-CRPC.

The term "metastasis-free survival" or "MFS" refers to the the percentage of subjects in a study who have survived without cancer spread for a defined period of time or death. MFS is usually reported as time from the beginning of treatment in the study. MFS is reported for an individual or a study population. In the context of treatment of NM-CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months.

The term "placebo" as used herein means administration of a pharmaceutical composition that does not include a second-generation anti-androgen. In the context of treatment of NM-CRPC, men that are administered an anti-androgen or placebo will need to continue to maintain castrated levels of testosterone by either coadministration of a GnRH agonist/antagonist or orchiectomy.

Routes of Administration

Suitable routes of administration of the anti-androgen include, but are not limited to, oral or parenteral (e.g., intravenous, subcutaneous, intramuscular). The anti-androgen is administered in the form of a dispersion, solution, suspension, tablet, capsule, or pill. All formulations for oral administration are in dosages suitable for such administration. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A therapeutically effective amount of an anti-androgen can vary widely depending on the severity of the disease, the age and relative health of the subject, the potency of the anti-androgen used and other factors.

The term "acceptable" with respect to a formulation, composition or ingredient, as used herein, means having no persistent detrimental effect on the general health of the male human being treated.

Methods of Dosing and Treatment Regimens

In one aspect, a second-generation anti-androgen is administered daily to men with NM-CRPC. In some embodiments, the second-generation anti-androgen is orally administered to men with NM-CRPC. In some embodiments, the second-generation anti-androgen is administered once-a-day to men with NM-CRPC. In some embodiments, the second-generation anti-androgen is administered twice-a-day to men with NM-CRPC. In some embodiments, the second-generation anti-androgen is administered three times-a-day to men with NM-CRPC.

In general, doses of a second-generation anti-androgen employed for treatment of NM-CRPC in adult male humans are typically in the range of 10 mg-1000 mg per day. In one embodiment, the desired dose is conveniently presented in a single dose or in divided doses administered simultaneously (or over a short period of time) or at appropriate intervals, for example as two, three, four or more sub-doses per day. In some embodiments, the second-generation anti-androgen is conveniently presented in divided doses that are administered simultaneously (or over a short period of time) once a day. In some embodiments, the second-generation anti-androgen is conveniently presented in divided doses that are administered in equal portions twice-a-day.

In some embodiments, the second-generation anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, about 480 mg per day, about 600 mg per day, about 780 mg per day, or about 960 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human with NM-CRPC at a dose of about 240 mg per day. In some embodiments, greater than 240 mg per day of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered to the male human with NM-CRPC. In some embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered once-a-day. In some other embodiments, the amount of 4-[7-(6-cyano-5-trifluoromethylpyridin-3-yl)-8-oxo-6-thioxo-5,7-diazaspiro[3.4]oct-5-yl]-2-fluoro-N-methylbenzamide is administered twice-a-day.

In some embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human with NM-CRPC at a dose of about 160 mg per day. In some embodiments, greater than 160 mg per day of 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human with NM-CRPC.

In certain embodiments wherein improvement in the status of the NM-CRPC in the male is not observed, the daily dose of the second-generation anti-androgen is increased. In some embodiments, a once-a-day dosing schedule is changed to a twice-a-day dosing schedule. In some embodiments, a three times a day dosing schedule is employed to increase the amount of second-generation anti-androgen that is administered.

In some embodiments, the amount of the second-generation anti-androgen that is given to the men with NM-CRPC varies depending upon factors such as, but not limited to, the particular second-generation anti-androgen, condition and severity of the NM-CRPC, and the identity (e.g., weight) of the man.

The following listing of Embodiments in intended to complement, rather than displace or supersede, the previous descriptions.

Embodiment 1

A method of treating non-metastatic castration-resistant prostate cancer in a male human comprising administering a therapeutically effective amount of an anti-androgen to a male human with a non-metastatic castration-resistant prostate cancer Embodiment 2

The method of Embodiment 1, wherein the non-metastatic castration-resistant prostate cancer is a high risk non-metastatic castration-resistant prostate cancer.

Embodiment 3

The method of Embodiment 2, wherein the male human with the high risk non-metastatic castration-resistant prostate cancer has a prostate-specific antigen doubling time (PSADT) that is less than or equal to 10 months.

Embodiment 4

The method of any one of Embodiments 1 to 3, wherein administration of the anti-androgen provides an increase in the metastasis-free survival of the male human.

Embodiment 5

A method of providing an increase in the metastasis-free survival of a male human with prostate cancer comprising administering administering a therapeutically effective amount of an anti-androgen to the male human with prostate cancer.

Embodiment 6

The method of Embodiment 5, wherein the prostate cancer is non-metastatic castration-resistant prostate cancer.

Embodiment 7

The method of Embodiment 5, wherein the prostate cancer is high risk non-metastatic castration-resistant prostate cancer.

Embodiment 8

The method of Embodiment 7, wherein the male human with high risk non-metastatic castration-resistant prostate cancer has a prostate-specific antigen doubling time (PSADT) that is less than or equal to 10 months.

Embodiment 9

The method of any one of Embodiments 1 to 8, wherein the anti-androgen is a non-steroidal anti-androgen.

Embodiment 10

The method of any one of Embodiments 1 to 9, wherein the anti-androgen binds directly to the ligand-binding domain of the androgen receptor.

Embodiment 11

The method of any one of Embodiments 1 to 10, wherein the anti-androgen is a second-generation anti-androgen.

Embodiment 12

The method of any one of Embodiments 1 to 11, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide; 4-(3-(4-cyano-3-(trifluoromethyl)phenyl)-5,5-dimethyl-4-oxo-2-thioxoimidazolidin-1-yl)-2-fluoro-N-methylbenzamide (enzalutamide); or 4-[7-(4-cyano-3-trifluoromethylphenyl)-8-oxo-6-thioxo-5,7-diazaspiro[3.4]oct-5-yl]-2-fluoro-N-methylbenzamide (RD162).

Embodiment 13

The method of any one of Embodiments 1 to 12, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

Embodiment 14

The method of Embodiment 13, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human.

Embodiment 15

The method of Embodiment 13 or 14, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human.

Embodiment 16

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day.

Embodiment 17

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day.

Embodiment 18

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day, about 60 mg per day, about 90 mg per day, about 120 mg per day, about 180 mg per day, about 240 mg per day, about 300 mg per day, about 390 mg per day, or about 480 mg per day.

Embodiment 19

The method of any one of Embodiments 13 to 15, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

Embodiment 20

The method of any one of Embodiments 13 to 19, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

EXAMPLES

These examples are provided for illustrative purposes only and not to limit the scope of the claims provided herein.

Example 1: Phase III Clinical Trial of 4-[7-(6-Cyano-5-trifluoromethylpyridin-3-yl)-8-oxo-6-thioxo-5,7-diazaspiro[3.4]oct-5-yl]-2-fluoro-N-methylbenzamide in Men with Non-Metastatic Castration-Resistant Prostate Cancer (NM-CRPC)

This is a randomized, multicenter, double-blind, Phase III clinical trial evaluating the efficacy and safety of 4-[7-(6-cyano-5-trifluoromethylpyridin-3-yl)-8-oxo-6-thioxo-5,7-diazaspiro[3.4]oct-5-yl]-2-fluoro-N-methylbenzamide (treatment arm A) versus placebo (treatment arm B) in men with high risk NM-CRPC, defined as PSA Doubling Time (PSADT) ≤10 months. All men participating in the clinical trial should maintain castrated levels of testosterone (<50 ng/dL [1.72 nmol/L]) by continuous administration of a GnRH agonist or antagonist, or by orchiectomy.

4-[7-(6-Cyano-5-trifluoromethylpyridin-3-yl)-8-oxo-6-thioxo-5,7-diazaspiro[3.4]oct-5-yl]-2-fluoro-N-methylbenzamide will be administered orally on a continuous daily dosing schedule, at a starting dose of 240 mg per day in treatment arm A. Matched placebo will be administered orally on a continuous daily dosing schedule, at a starting dose of 240 mg per day in treatment arm B.

Patients will be followed for safety and efficacy as per the schedule of assessments and will remain on study treatment until documented progression (development of metastases as assessed by blinded independent central review) or unacceptable toxicity.

Patients discontinuing treatment due to disease progression will be followed for survival and subsequent anticancer therapies every 4 months until death, loss of follow-up, or withdrawal of consent, whichever comes first.

Patients discontinuing treatment prior to disease progression will continue to have scheduled disease assessments until progression, initiation of a subsequent anticancer therapy in the absence of documented disease progression, withdrawal of consent, loss of follow-up, or until death, whichever comes first.

Endpoints

The primary endpoint is metastasis-free survival (MFS).

The secondary endpoints include overall survival (OS); time to metastasis (TTM); progression-free survival (PFS); health-related quality of life and prostate cancer-specific symptoms; type, incidence, severity, timing, seriousness, and relatedness of adverse events and laboratory abnormalities; pharmacokinetics parameters.

Target Population

Inclusion Criteria

1. Histologically or cytologically confirmed adenocarcinoma of the prostate without neuroendocrine differentiation or small cell features, with high risk for development of metastases, defined as PSADT ≤10 months
2. Castration-resistant prostate cancer demonstrated during continuous androgen deprivation therapy (ADT)/post orchiectomy, defined as 3 consecutive rises of PSA, 1 week apart, resulting in two 50% increases over the nadir, with the last PSA >2 ng/mL
3. Maintain castrate levels of testosterone (<50 ng/dL [1.72 nmol/L]) within 4 weeks of randomization and throughout the study
4. Patients currently receiving bone loss prevention treatment with bone-sparing agents (e.g., bisphosphonates, denosumab [Prolia®]) must be on stable doses for at least 4 weeks prior to randomization
5. Patients who received a first generation anti-androgen (e.g., bicalutamide, flutamide, nilutamide) as part of an initial combined androgen blockade therapy or as second-line hormonal therapy must show continuing disease (PSA) progression off the anti-androgen for at least 4 weeks prior to randomization
6. At least 4 weeks must have elapsed from the use of 5-α reductase inhibitors (e.g., dutasteride, finasteride, aminoglutethamide), estrogens, and any other anti-cancer therapy prior to randomization, including chemotherapy given in the adjuvant/neoadjuvant setting (e.g., clinical trial)
7. At least 4 weeks must have elapsed from major surgery or radiation therapy prior to randomization
8. Age ≥18 years
9. Eastern Cooperative Oncology Group (ECOG) Performance Status 0 or 1
10. Resolution of all acute toxic effects of prior therapy or surgical procedure to Grade ≤1 or baseline prior to randomization
11. Adequate organ function as defined by the following criteria:
    - Serum aspartate transaminase (AST; serum glutamic oxaloacetic transaminase [SGOT]) and serum alanine transaminase (ALT; serum glutamic pyruvic transaminase [SGPT]) ≤2.5× upper limit of normal (ULN)
    - Total serum bilirubin ≤1.5×ULN
    - Serum creatinine ≤2×ULN
    - Absolute neutrophil count (ANC) ≥1500/μL
    - Platelets ≥100,000/μL
    - Hemoglobin ≥9.0 g/dL
    - Administration of growth factors or blood transfusions will not be allowed within 4 weeks of the hematology labs required to confirm eligibility
12. Signed and dated informed consent document indicating that the patient (or legally acceptable representative) has been informed of all pertinent aspects of the trial prior to randomization
13. Willingness and ability to comply with scheduled visits, treatment plans, laboratory and radiographic assessments, and other study procedures, including ability to swallow large capsules, the completion of patient reported outcomes questionnaires and long-term survival follow-up visits Exclusion Criteria 1. Presence of distant metastases, including CNS and vertebral or meningeal involvement. Exception: pelvic lymph nodes <2 cm in short axis (N1) located below the iliac bifurcation are allowed
2. Symptomatic loco-regional disease requiring medical intervention, such as moderate or severe urinary obstruction or hydronephrosis due to primary tumor (e.g., tumor obstruction of bladder trigone)
3. Prior treatment with second-generation antiandrogens (e.g., enzalutamide)
4. Prior treatment with CYP17 inhibitors (e.g., abiraterone acetate, orteronel, galeterone, ketoconazole)

5. Prior treatment with radiopharmaceutical agents (e.g., Strontium-89), immunotherapy (e.g., sipuleucel-T) or any other investigational agent for NM-CRPC
6. Prior chemotherapy, except if administered in the adjuvant/neoadjuvant setting
7. History of seizure or condition that may pre-dispose to seizure (e.g., prior stroke within 1 year prior to randomization, brain arteriovenous malformation, Schwannoma, meningioma, or other benign CNS or meningeal disease which may require treatment with surgery or radiation therapy)
8. Concurrent therapy with any of the following (all must have been discontinued or substituted for at least 4 weeks prior to randomization):
   Medications known to lower the seizure threshold
   Herbal and non-herbal products that may decrease PSA levels (i.e., saw palmetto, pomegranate juice)
   Systemic (oral/IV/IM) corticosteroids. Short term use (≤4 weeks) of corticosteroids during the study is allowed if clinically indicated, but it should be tapered off as soon as possible
   Any other experimental treatment on another clinical trial
9. History or evidence of any of the following conditions:
   Any prior malignancy (other than adequately treated basal cell or squamous cell skin cancer, superficial bladder cancer, or any other cancer in situ currently in complete remission) within 5 years prior to randomization
   Severe/unstable angina, myocardial infarction, symptomatic congestive heart failure, arterial or venous thromboembolic events (e.g., pulmonary embolism, cerebrovascular accident including transient ischemic attacks), or clinically significant ventricular arrhythmias within 6 months prior to randomization
   Uncontrolled hypertension (≥160 mmHg systolic blood pressure and/or diastolic blood pressure ≥100 mmHg)
   Gastrointestinal disorder affecting absorption
   Active infection, such as human immunodeficiency virus (HIV)
   Any other condition that, in the opinion of the Investigator, would impair the patient's ability to comply with study procedures Assessment Schedule Safety Assessment Plan Patients will be assessed for adverse events at each monthly clinic visit while on the study. Adverse events will be graded according to the NCI Common Terminology Criteria for Adverse Events (CTCAE) Version 4.0. Adverse events will be assessed by the investigator as related or not related to study drug. Dose interruptions and/or reductions to the next lower dose level will be permitted as needed, provided that study discontinuation criteria have not been met (e.g., documented disease progression or unacceptable toxicity, such as seizure).

An independent third-party Data Monitoring Committee (DMC) will monitor the safety of the patients, with meetings at least twice per year to determine overall safety and benefit:risk assessment. Periodic quarterly adverse event data review will also be performed by designated members of the sponsor's primary study team and will be blinded to treatment assignment with adverse event from both treatment groups combined. Any safety issues of concern identified by the primary study team will be promptly reported to the DMC, as per the DMC charter.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed is:

1. A method of treating a male human with non-metastatic castration-resistant prostate cancer, the method comprising administering an anti-androgen at a dose of about 30 mg per day to about 480 mg per day to a male human in need of such treatment, wherein the anti-androgen is:

4-[7-(6-cyano-5-trifluoromethylpyridin-3-yl)-8-oxo-6-thioxo-5,7-diazaspiro[3.4]oct-5-yl]-2 fluoro-N-methylbenzamide,

[4-(3-(4-cyano-3-(trifluoromethyl)phenyl)-5,5-dimethyl-4-oxo-2-thioxoimidazolidin-1-yl)-2-fluoro-N-methylbenzamide, or 4-[7-[4-cyano-3-(trifluoromethyl)phenyl]-8-oxo-6-thioxo-5,7-diazaspiro[3.4]oct-5-yl]-2-fluoro-N-methylbenzamide;]

wherein said method further comprises administering a gonadotropin releasing hormone (GnRH) agonist.

2. The method of claim 1, wherein the non-metastatic castration-resistant prostate cancer is a high risk non-metastatic castration-resistant prostate cancer.

[3. The method of claim 1, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.]

4. The method of claim [3] *1*, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered daily to the male human.

5. The method of claim [3] *1*, wherein 4-[7-(6-cyano-5-trifluoromethylpyridin-3-yl)-8-oxo-6-thioxo-5, 7-diazaspiro[3.4]oct-5-yl]-2-fluoro-N-methylbenzamide (ARN-509) is administered orally to the male human at a dose of about 180 mg per day to about 480 mg per day.

6. The method of claim [3] *1*, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide (ARN-509) is administered orally to the male human at a dose of:

(a) about 30 mg per day;
(b) about 60 mg per day;
(c) about 90 mg per day;
(d) about 120 mg per day; or
(e) about 240 mg per day.

7. The method of claim [3] *1*, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosage schedule.

8. The method of claim [3] *1*, wherein the GnRH agonist is leuprolide, buserelin, naferelin, histrelin, goserelin or deslorelin.

[9. The method of claim 1, wherein the anti-androgen is 4-(3-(4-cyano-3-(trifluoromethyl)phenyl)-5,5-dimethyl-4-oxo-2-thioxoimidazolidin-1-yl)-2-fluoro-N-methylbenzamide.]

[10. The method of claim 9, wherein the GnRH agonist is leuprolide, buserelin, naferelin, histrelin, goserelin or deslorelin.]

[11. The method of claim 1, wherein the anti-androgen is 4-[7-[4-cyano-3-(trifluoromethyl)phenyl]-8-oxo-6-thioxo-5,7-diazaspiro[3.4]oct-5-yl]-2-fluoro-N-methylbenzamide.]

[12. The method of claim 11, wherein the GnRH agonist is leuprolide, buserelin, naferelin, histrelin, goserelin or deslorelin.]

13. The method of claim 1, wherein the anti-androgen is administered orally to the male human.

14. A method of treating a male human with non-metastatic castration-resistant prostate cancer, the method consisting essentially of administering an anti-androgen at a dose of about 30 mg per day to about 480 mg per day to a male human in need of such treatment, wherein the anti-androgen is:

4-[7-(6-cyano-5-trifluoromethylpyridin-3-yl)-8-oxo-6-thioxo-5,7-diazaspiro[3.4]oct-5-yl]-2 fluoro-N-methylbenzamide,

[4-(3-(4-cyano-3-(trifluoromethyl)phenyl)-5,5-dimethyl-4-oxo-2-thioxoimidazolidin-1-yl)-2-fluoro-N-methylbenzamide, or 4-[7-[4-cyano-3-(trifluoromethyl)phenyl]-8-oxo-6-thioxo-5,7-diazaspiro[3.4]oct-5-yl]-2-fluoro-N-methylbenzamide;]

wherein said method further comprises administering a gonadotropin releasing hormone (GnRH) agonist.

[15. The method of claim 14, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.]

16. The method of claim [15] *14*, wherein the GnRH agonist is leuprolide, buserelin, naferelin, histrelin, goserelin or deslorelin.

17. The method of claim [15] *14*, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide (ARN-509) is administered orally to the male human at a dose of:

(a) about 30 mg per day;

(b) about 60 mg per day;

(c) about 90 mg per day;

(d) about 120 mg per day; or (e) about 240 mg per day.

[18. The method of claim 9, wherein the 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human at a dose of about 160 mg per day.]

19. The method of claim [3] *1*, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

20. The method of claim [3] *1*, wherein the GnRH agonist is leuprolide.

21. The method of claim [3] *1*, wherein the GnRH agonist is buserelin.

22. The method of claim [3] *1*, wherein the GnRH agonist is naferelin.

23. The method of claim [3] *1*, wherein the GnRH agonist is histrelin.

24. The method of claim [3] *1*, wherein the GnRH agonist is goserelin.

25. The method of claim [3] *1*, wherein the GnRH agonist is deslorelin.

*26. A method of treating a male human with non-metastatic castration-resistant prostate cancer, the method comprising administering an anti-androgen at a dose of about 30 mg per day to about 480 mg per day to a male human in need of such treatment, wherein the anti-androgen is:*

*4-(3-(4-cyano-3-(trifluoromethyl)phenyl)-5,5-dimethyl-4-oxo-2-thioxoimidazolidin-1-yl)-2-fluoro-N-methylbenzamide,*

*wherein said method further comprises administering a gonadotropin releasing hormone (GnRH) agonist.*

*27. The method of claim 26, wherein the non-metastatic castration-resistant prostate cancer is a high risk non-metastatic castration-resistant prostate cancer.*

*28. The method of claim 26, wherein 4-(3-(4-cyano-3-(trifluoromethyl)phenyl)-5,5-dimethyl-4-oxo-2-thioxoimidazolidin-1-yl)-2-fluoro-N-methylbenzamide is administered daily to the male human.*

*29. The method of claim 26, wherein 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human on a continuous daily dosage schedule.*

*30. The method of claim 26, wherein the GnRH agonist is leuprolide, buserelin, naferelin, histrelin, goserelin or deslorelin.*

*31. The method of claim 26, wherein the anti-androgen is administered orally to the male human.*

*32. The method of claim 26, wherein the GnRH agonist is leuprolide.*

*33. The method of claim 26, wherein the GnRH agonist is buserelin.*

*34. The method of claim 26, wherein the GnRH agonist is naferelin.*

*35. The method of claim 26, wherein the GnRH agonist is histrelin.*

*36. The method of claim 26, wherein the GnRH agonist is goserelin.*

*37. The method of claim 26, wherein the GnRH agonist is deslorelin.*

*38. The method of claim 26, wherein the 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human at a dose of about 160 mg per day.*

*39. A method of treating a male human with non-metastatic castration-resistant prostate cancer, the method consisting essentially of administering an anti-androgen at a dose of about 30 mg per day to about 480 mg per day to a male human in need of such treatment, wherein the anti-androgen is:*

*4-(3-(4-cyano-3-(trifluoromethyl)phenyl)-5,5-dimethyl-4-oxo-2-thioxoimidazolidin-1-yl)-2-fluoro-N-methylbenzamide,*

*wherein said method further comprises administering a gonadotropin releasing hormone (GnRH) agonist.*

*40. The method of claim 39, wherein the GnRH agonist is leuprolide, buserelin, naferelin, histrelin, goserelin or deslorelin.*

*41. The method of claim 39, wherein the 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human at a dose of about 160 mg per day.*

*42. A method of treating a male human with non-metastatic castration-resistant prostate cancer, the method comprising administering an anti-androgen at a dose of about*

*30 mg per day to about 480 mg per day to a male human in need of such treatment, wherein the anti-androgen is:*

*4-[7-[4-cyano-3-(trifluoromethyl)phenyl]-8-oxo-6-thioxo-5,7-diazaspiro[3.4]oct-5-yl]-2-fluoro-N-methylbenzamide,*

*wherein said method further comprises administering a gonadotropin releasing hormone (GnRH) agonist.*

*43. The method of claim 42, wherein the non-metastatic castration-resistant prostate cancer is a high risk non-metastatic castration-resistant prostate cancer.*

*44. The method of claim 42, wherein 4-[7-[4-cyano-3-(trifluoromethyl)phenyl]-8-oxo-6-thioxo-5,7-diazaspiro[3.4]oct-5-yl]-2-fluoro-N-methylbenzamide is administered daily to the male human.*

*45. The method of claim 42, wherein 4-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human on a continuous daily dosage schedule.*

*46. The method of claim 42, wherein the GnRH agonist is leuprolide, buserelin, naferelin, histrelin, goserelin or deslorelin.*

*47. The method of claim 42, wherein the anti-androgen is administered orally to the male human.*

*48. The method of claim 42, wherein the GnRH agonist is leuprolide.*

*49. The method of claim 42, wherein the GnRH agonist is buserelin.*

*50. The method of claim 42, wherein the GnRH agonist is naferelin.*

*51. The method of claim 42, wherein the GnRH agonist is histrelin.*

*52. The method of claim 42, wherein the GnRH agonist is goserelin.*

*53. The method of claim 42, wherein the GnRH agonist is deslorelin.*

*54. A method of treating a male human with non-metastatic castration-resistant prostate cancer, the method consisting essentially of administering an anti-androgen at a dose of about 30 mg per day to about 480 mg per day to a male human in need of such treatment, wherein the anti-androgen is:*

*4-[7-[4-cyano-3-(trifluoromethyl)phenyl]-8-oxo-6-thioxo-5,7-diazaspiro[3.4] oct-5-yl]-2-fluoro-N-methylbenzamide,*

*wherein said method further comprises administering a gonadotropin releasing hormone (GnRH) agonist.*

*55. The method of claim 54, wherein the GnRH agonist is leuprolide, buserelin, naferelin, histrelin, goserelin or deslorelin.*

* * * * *